US012674971B2

(12) United States Patent
Takada et al.

(10) Patent No.: US 12,674,971 B2
(45) Date of Patent: Jul. 7, 2026

(54) OBJECTIVE OPTICAL SYSTEM FOR ENDOSCOPE AND ENDOSCOPE HAVING SAME

(71) Applicant: OLYMPUS CORPORATION, Hachioji (JP)

(72) Inventors: Keisuke Takada, Kokubunji (JP); Keisuke Ichikawa, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 264 days.

(21) Appl. No.: 18/650,671

(22) Filed: Apr. 30, 2024

(65) Prior Publication Data

US 2025/0334790 A1       Oct. 30, 2025

Related U.S. Application Data

(63) Continuation of application No. PCT/JP2021/044479, filed on Dec. 3, 2021.

(51) Int. Cl.
*G02B 23/24*       (2006.01)
*A61B 1/00*        (2006.01)
*G02B 9/12*        (2006.01)

(52) U.S. Cl.
CPC ............. *G02B 23/243* (2013.01); *G02B 9/12* (2013.01); *A61B 1/0019* (2013.01)

(58) Field of Classification Search
CPC ........ G02B 23/243; G02B 9/12; A61B 1/0019
(Continued)

(56) References Cited

U.S. PATENT DOCUMENTS 8,203,798 B2       6/2012  Takato
9,568,726 B2       2/2017  Kamo et al.
(Continued)

FOREIGN PATENT DOCUMENTS

JP       4819969 B2       11/2011
JP       5930257 B1       6/2016
(Continued)

OTHER PUBLICATIONS

International Preliminary Report on Patentability (IPRP) (and English language translation thereof) dated Jun. 13, 2024, issued in counterpart International Application No. PCT/JP2021/044479.
(Continued)

*Primary Examiner* — Sharrief I Broome
(74) *Attorney, Agent, or Firm* — Holtz, Holtz & Volek PC

(57)       ABSTRACT

An objective optical system for an endoscope comprising, in order from the object side, a first lens unit G1 having a negative refractive power, a second lens unit G2 having a positive refractive power, and a third lens unit G3 having a positive refractive power. The first lens unit G1 includes a negative lens L1. The second lens unit G2 includes a positive meniscus lens L2 having a convex surface facing the image side. The third lens unit G3 includes, in order from the object side, an object side positive lens L3 and a cemented lens CL made up of a positive lens L4 and a negative lens L5. The second lens unit G2 is moved for focusing. The objective optical system satisfies the following conditional expressions (1) and (2):

$$-0.07 < f1/f2 < -0.015 \tag{1}$$

$$-0.4 < f1/f3 < -0.15 \tag{2}$$

(Continued)

where f1 is the focal length of the first lens unit, f2 is the focal length of the second lens unit, and f3 is the focal length of the third lens unit.

13 Claims, 16 Drawing Sheets

(58) Field of Classification Search
USPC ........................................................ 359/784
See application file for complete search history.

(56)                   References Cited

U.S. PATENT DOCUMENTS

| | | | |
|---|---|---|---|
| 9,817,226 | B2 | 11/2017 | Noguchi |
| 10,018,827 | B2 | 7/2018 | Ushio |
| 11,576,564 | B2 | 2/2023 | Kawakami |
| 2011/0211267 | A1 | 9/2011 | Takato |
| 2016/0327780 | A1 | 11/2016 | Kamo et al. |
| 2017/0071449 | A1 | 3/2017 | Noguchi |
| 2017/0343790 | A1 | 11/2017 | Ushio |
| 2019/0261834 | A1 | 8/2019 | Kawakami |
| 2021/0239950 | A1 | 8/2021 | Ichikawa et al. |
| 2022/0019072 | A1 | 1/2022 | Takato |

FOREIGN PATENT DOCUMENTS

| | | | |
|---|---|---|---|
| JP | 6001229 | B2 | 10/2016 |
| JP | 2017219783 | A | 12/2017 |
| WO | 2016204001 | A1 | 12/2016 |
| WO | 2018116865 | A1 | 6/2018 |
| WO | 2020178884 | A1 | 9/2020 |
| WO | 2020217443 | A1 | 10/2020 |

OTHER PUBLICATIONS

International Search Report (ISR) (and English language translation thereof) dated Jan. 11, 2022 issued in International Application No. PCT/JP2021/044479.

Written Opinion dated Jan. 11, 2022 issued in International Application No. PCT/JP2021/044479.

435.84 ————
656.27 --------
587.56 ————

SA
FNO 3.620

AS
IH 0.50

DT
IH 0.50

CC
IH 0.50

SA
FNO 3.622

AS
IH 0.50

DT
IH 0.50

CC
IH 0.50 r1  r2  r3  r4  r5  r6 (r7)  r8 r9  r10  r11  r12  r13  r14 r15

S d1 d2  d3  d4  d5 d6  d7  d8  d9  d10  d11  d12  d13 d14 d15

G1     G2         G3

L1  F   L2   S L3   L4   L5   L6  CG

OBJECTIVE OPTICAL SYSTEM FOR ENDOSCOPE AND ENDOSCOPE HAVING SAME

CROSS REFERENCE TO RELATED APPLICATION

The present application is a continuation application of PCT/JP2021/44479 filed on Dec. 3, 2021; the entire contents of which are incorporated herein by reference.

BACKGROUND OF THE INVENTION

Field of the Invention

The present invention relates to an objective optical system for an endoscope and an endoscope having the same.

Description of the Related Art

Medical endoscopes are desired to be able to capture high quality images of relatively far objects and relatively near objects in order to improve their observation performance. To improve operability and to reduce examinee's discomfort, it is desired that the diameter of the insert part of medical endoscopes be small. For these reasons, objective optical systems for endoscopes are desired to be small and to have a focusing function.

For example, endoscope objective optical systems having a focusing function are discloses in Japanese Patent No. 4819969, Japanese Patent No. 5930257, Japanese Patent No. 6001229, Japanese Patent Application Laid-Open No. 2017-219783, and WO2020/217443. The endoscope optical systems disclosed in these literatures includes, in order from the object side, a first lens unit having a negative refractive power, a second lens unit having a positive refractive power, and a third lens unit having a positive refractive power. They can be focused on both far objects and near objects by moving the second lens unit.

SUMMARY OF THE INVENTION

An objective optical system for an endoscope according to at least some embodiments of the present invention comprises, in order from the object side:

a first lens unit having a negative refractive power;

a second lens unit having a positive refractive power; and a third lens unit having a positive refractive power, wherein the first lens unit includes a negative lens, the second lens unit includes a positive meniscus lens having a convex surface facing the image side, the third lens unit includes, in order from the object side, an object side positive lens and a cemented lens made up of a positive lens and a negative lens, the second lens unit is moved for focusing, and the objective optical system for an endoscope satisfies the following conditional expressions (1) and (2):

$$-0.07 < f1/f2 < -0.015 \quad (1)$$

$$-0.4 < f1/f3 < -0.15 \quad (2)$$

where f1 is the focal length of the first lens unit, f2 is the focal length of the second lens unit, and f3 is the focal length of the third lens unit.

An endoscope according to at least some embodiments of the present invention is characterized by comprising the objective optical system for an endoscope described above.

DETAILED DESCRIPTION OF THE INVENTION

Figure 1A:
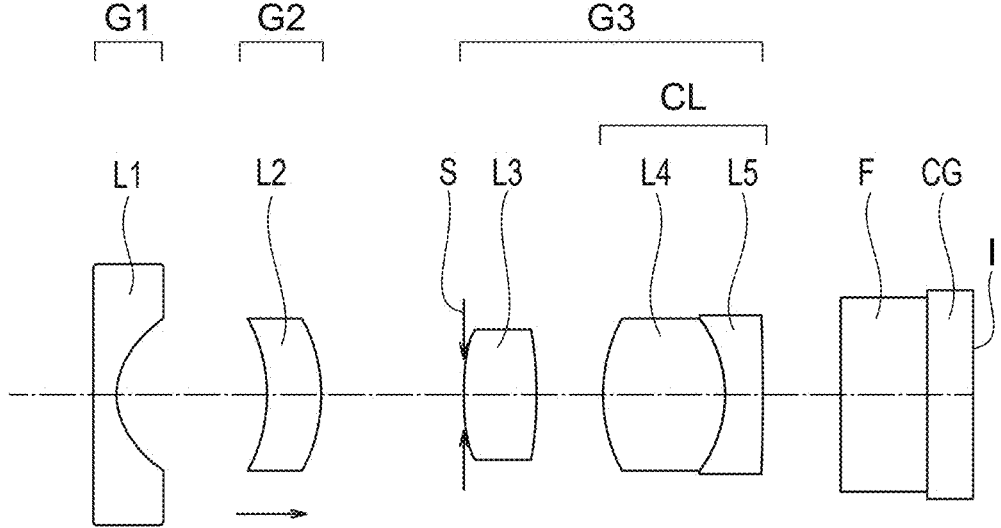
FIGS. 1A and 1B are cross sectional views of the endoscope objective optical system according to an embodiment.

An objective optical system for an endoscope (which will also be referred to as "endoscope objective optical system" hereinafter) and an endoscope according to an embodiment will be described in the following in terms of the reason why they are configured as described and their operations with reference to the drawings. It should be understood that the present invention is not limited by the embodiment.

An endoscope objective optical system according to an embodiment includes, in order from the object side, a first lens unit having a negative refractive power, a second lend unit having a positive refractive power, and a third lens unit having a positive refractive power. The first lens unit includes a negative lens. The second lens unit includes a positive meniscus lens having a convex surface facing the image side. The third lens unit includes, in order from the object side, an object side positive lens and a cemented lens made up of a positive lens and a negative lens. The second lens unit is moved for focusing. The endoscope objective optical system satisfies the following conditional expressions (1) and (2):

$$-0.07 < f1/f2 < -0.015 \qquad (1)$$

$$-0.4 < f1/f3 < -0.15 \qquad (2)$$

where f1 is the focal length of the first lens unit, f2 is the focal length of the second lens unit, and f3 is the focal length of the third lens unit.

Retro-focus optical systems can have a long back focus. The endoscope objective optical system according to the embodiment includes, in order from the object side, the first lens unit having a negative refractive power and the second unit having a positive refractive power. This means that the first lens unit and the second lens unit constitute a retro-focus optical system. Therefore, it is possible to provide a large space on the image side of the second lens unit. A large space available on the image side of the second lens unit allows the second lens unit to move along the optical axis without difficulty.

The endoscope objective optical system according to the embodiment includes the third lens unit disposed on the image side of the second lens unit. A large space available on the image side of the second lens unit allows the third lens unit to be provided without difficulty.

An imager may be provided at the location of the image surface. When this is the case, the endoscope objective optical system and the imager constitute an imaging unit. The assembly of the imaging unit involves alignment of the image surface and the imaging surface of the imager. A large space available on the image side of the second lens unit makes the alignment easy.

The first lens unit in the endoscope objective optical system according to the embodiment includes a negative lens, and the second lens unit includes a positive meniscus lens having a convex surface facing the image side. Therefore, the first lens unit has a negative refractive power, and the second lens unit has a positive refractive power. Thus, they can constitute a retro-focus optical system.

It is preferred that the number of lenses in the first lens unit and the number of lenses in the second lens unit be each one. Constituting each lens unit by one lens can make the optical system small.

As described above, the second lens unit includes a positive meniscus lens having a convex surface facing the image side. The principal point of the positive meniscus lens having a convex surface facing the image side is located on the image side of its image side lens surface. Therefore, it is possible to provide a large space on the image side of the second lens unit. This allows the second lens unit to be moved and the third lens unit to be provided without difficulty.

The third lens unit in the endoscope objective optical system according to the embodiment includes, in order from the object side, an object side positive lens and a cemented lens. The cemented lens is made up of a positive lens and a negative lens. Using a positive lens and a cemented lens in the third lens unit allows favorable correction of spherical aberration and chromatic aberration. As a result, it is possible to provide an endoscope objective optical system with favorably corrected aberrations.

As described above, it is preferred that the first lens unit and the second lens unit be each composed of a single lens. When this is the case, it is difficult to correct aberrations in each lens unit. By using a positive lens and a cemented lens in the third lens unit, it is possible to favorably correct aberrations generated in the first lens unit and the second lens unit.

Conditional expression (1) limits the ratio of the refractive power of the first lens unit and the refractive power of the second lens unit. Conditional expression (1) is relevant to favorable correction of aberrations and downsizing of the optical system. Satisfying conditional expression (1) allows favorable correction of aberrations and downsizing of the optical system.

When the value of f1/f2 falls below the lower bound of conditional expression (1), the refractive power of the first lens unit is too low or the refractive power of the second lens unit is too high. When the refractive power of the first lens unit is too low, the ray height incident on the first lens unit is high. This leads to an increase in the outer diameter of the first lens unit. As described above, the first lens unit includes a negative lens, and an increased diameter of the negative lens will result.

When the refractive power of the second lens unit is too high, the sensitivity to decentering of the second lens unit is high. When the decentering sensitivity is high, deterioration in the imaging performance resulting from decentering of the lens unit is large. When the decentering sensitivity of the second lens is high, a decentering between the second lens unit and another lens unit will result in a large deterioration in the imaging performance. As described above, the second lens unit is moved for focusing. Therefore, if the imaging performance is deteriorated largely by decentering, it is difficult to maintain high imaging performance when in focus.

When the value of f1/f2 exceeds the upper bound of conditional expression (1), the refractive power of the first lens unit is too high or the refractive power of the second lens unit is too low. When the refractive power of the first lens unit is too high, the imaging position of the first lens unit shifts toward the image surface. This results in an increase in the entire length of the optical system and an increase in the size of the optical system. Moreover, the Petzval sum will increase, leading to a large curvature of the image surface toward the image side.

When the refractive power of the second lens unit is too low, the amount of movement of the second lens unit is necessitated to be large. This leads to an increase in the entire length of the optical system and an increase in the size of the optical system. Therefore, it is undesirable that the value of f1/f2 exceeds the upper bound of conditional expression (1).

Conditional expression (2) limits the ratio of the refractive power of the first lens unit and the refractive power of the third lens unit. Conditional expression (2) is relevant to favorable correction of aberrations. When conditional expression (2) is satisfied, aberrations can be favorably corrected, especially curvature of field can be favorably corrected.

When the value of f1/f3 falls below the lower bound of conditional expression (2), a large curvature of the image surface toward the object side will result. Then, the optical image will be blurred when in focus in either the central or peripheral portion thereof. Therefore, it is undesirable that the value of f1/f3 falls below the lower bound of conditional expression (2).

When the value of f1/f3 exceeds the upper bound of conditional expression (2), a large curvature of the image surface toward the image side will result. Then, the optical image will be blurred when in focus in either the central or peripheral portion thereof. Therefore, it is undesirable that the value of f1/f3 exceeds the upper bound of conditional expression (2).

The endoscope objective optical system according the embodiment can be focused on relatively far objects as well as relatively near objects. When conditional expression (2) is not satisfied, even if it is possible to make the curvature of field small when the optical system is focused on an object at either one of a far distance and a near distance, it is not possible to make it small when the optical system is focused on an object at the other distance.

It is more preferred that the following conditional expression (1') be satisfied instead of conditional expression (1):

$$-0.068 < f1/f2 < -0.025. \qquad (1')$$

It is more preferred that the following conditional expression (1") be satisfied instead of conditional expression (1):

$$-0.065 < f1/f2 < -0.028. \qquad (1'')$$

It is more preferred that the following conditional expression (2') be satisfied instead of conditional expression (2):

$$-0.39 < f1/f3 < -0.25. \qquad (2')$$

It is more preferred that the following conditional expression (2") be satisfied instead of conditional expression (2):

$$-0.385 < f1/f3 < -0.26. \qquad (2'')$$

An optical filter may be provided in the endoscope objective optical system according to the embodiment. In the case where the first lens unit and the second lend unit are each composed of a single lens, the optical filter may be provided between the first lens unit and the second lens unit, between the second lens unit and the third lens unit, in the third lens unit, or between the third lens unit and the image plane.

Figure 1B:
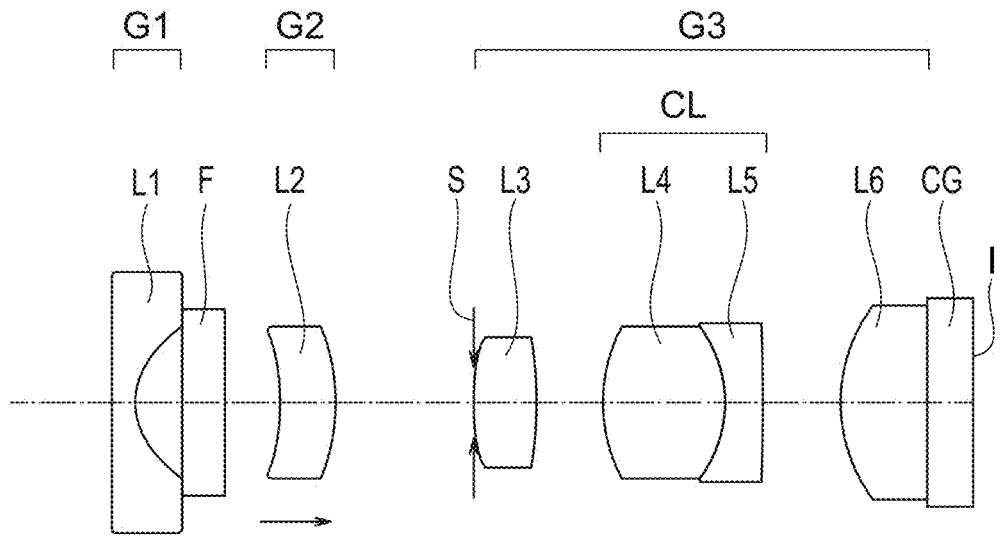

FIGS. 1A and 1B are cross sectional views of the endoscope objective optical system according to the embodiment. FIG. 1A is a cross sectional view of a first exemplary endoscope objective optical system according to the embodiment. FIG. 1B is a cross sectional view of a second exemplary endoscope objective optical system according to the embodiment. FIGS. 1A and 1B are cross sectional views of the lenses in the state in which the endoscope objective optical systems are focused on an object at a far distance.

As shown in FIG. 1A, the first exemplary endoscope objective optical system includes, in order from the object side, a first lens unit G1 having a negative refractive power, a second lens unit G2 having a positive refractive power, and a third lens unit G3 having a positive refractive power.

The first lens unit G1 includes a negative lens L1. The second lens unit G2 includes a positive meniscus lens L2 having a convex surface facing the image side. The third lens unit G3 includes, in order from the object side, an object side positive lens L3 and a cemented lens CL. The cemented lens CL is made up of a positive lens L4 and a negative lens L5.

Focusing is performed by moving the second lens unit G2. Specifically, when focusing is changed from far distance object to near distance object, the second lens unit G2 moves toward the image side.

The first exemplary endoscope objective optical system has an aperture stop S disposed between the second lens unit G2 and the third lens unit G3. More specifically, the aperture stop S is disposed at the apex of the object side surface of the object side positive lens L3.

The first exemplary endoscope objective optical system further includes a plane parallel plate F and a cover glass CG. For example, the plane parallel plate F is an optical filter. For example, the cover glass CG is a cover glass of an imager. The cover glass CG is cemented to the plane parallel plate F.

As shown in FIG. 1B, the second exemplary endoscope objective optical system includes, in order from the object side, a first lens unit G1 having a negative refractive power, a second lens unit G2 having a positive refractive power, and a third lens unit G3 having a positive refractive power.

The first lens unit G1 includes a negative lens L1. The second lens unit G2 includes a positive meniscus lens L2 having a convex surface facing the image side. The third lens unit G3 includes, in order from the object side, an object side positive lens L3, a cemented lens CL, and an image side positive lens L6. The cemented lens CL is made up of a positive lens L4 and a negative lens L5.

Focusing is performed by moving the second lens unit G2. Specifically, when focusing is changed from far distance object to near distance object, the second lens unit G2 moves toward the image side.

The second exemplary endoscope objective optical system has an aperture stop S disposed between the second lens unit G2 and the third lens unit G3. More specifically, the aperture stop S is disposed at the apex of the object side surface of the object side positive lens L3.

The second exemplary endoscope objective optical system further includes a plane parallel plate F disposed between the first lens unit G1 and the second lens unit G2. For example, the plane parallel plate F is an optical filter. The second exemplary endoscope objective optical system further includes a cover glass CG disposed on the image side of the third lens unit G3. For example, the cover glass CG is a cover glass of an imager. The cover glass CG is cemented to the image side positive lens L6.

It is preferred that the endoscope objective system according to the embodiment satisfy the following conditional expression (3):

$$-1.13 < f1/d23e < -0.4, \qquad (3)$$

where f1 is the focal length of the first lens unit, and d23e is the distance between the second lens unit and the third lens unit in the state in which the optical system is focused on an object at a far distance.

As described above, the first lens unit and the second lens unit in the endoscope objective optical system according to the embodiment constitute a retro-focus optical system. This ensures to provide a long back focus.

To further increase the back focus, it is effective to increase the negative refractive power of the first lens unit. However, increasing the negative refractive power of the first lens unit may result in increased chromatic aberration and coma in some cases. To avoid this, it is preferred to the first lens unit to have an appropriately refractive power of. As described above, the first lens unit includes a negative lens, and it is preferred to design the negative lens to have an appropriate refractive power.

The second lens unit in the endoscope objective optical system according to the embodiment is moved for focusing. Therefore, it is necessary to provide an adequate distance between the second lens unit and the third lens unit. This distance will also be referred to as the "lens unit distance" hereinafter. By appropriately setting the lens unit distance, it is possible to favorably correct chromatic aberration of magnification with the third lens unit.

By appropriately setting the negative refractive power of the first lens unit and the aforementioned lens unit distance, it is possible to accomplish balanced correction of aberrations of the entire optical system even in the case where the F-number of the optical system is small.

Conditional expression (3) limits the ratio of the focal length of the first lens unit and the aforementioned lens unit distance in the state in which the optical system is focused on an object at a far distance. When conditional expression (3) is satisfied, it is possible to accomplish downsizing of the optical system and favorable correction of chromatic aberration and coma.

When the value of f1/d23e falls below the lower bound of conditional expression (3), the negative refractive power of the first lens unit is too low or the lens unit distance in the state in which the optical system is focused on an object at a far distance is too short. When the negative refractive power of the first lens unit is too low, the size of the first lens unit is necessitated to be large. When the lens unit distance in the state in which the optical system is focused on an object at a far distance is too short, it is difficult to move the second lens unit sufficiently.

When the value of f1/d23e exceeds the upper bound of conditional expression (3), the negative refractive power of the first lens unit G1 is too high. This will result in increased chromatic aberration and coma.

It is more preferred that the following conditional expression (3') be satisfied instead of conditional expression (3):

$$-1.1 < f1/d23e < -0.45. \tag{3'}$$

It is more preferred that the following conditional expression (3") be satisfied instead of conditional expression (3):

$$-1.08 < f1/d23e < -0.46, \tag{3''}$$

It is preferred that the endoscope objective optical system according to the embodiment satisfy the following conditional expression (4):

$$-0.59 < f12e/f3' < -0.35, \tag{4}$$

where f12e is the combined focal length of the first lens unit and the second lens unit in the state in which the optical system is focused on an object at a far distance, and f3' is the combined focal length of the object side positive lens and the cemented lens.

Conditional expression (4) limits the ratio of the two composite focal lengths, one of which is the combined focal length of the first lens unit and the second lens unit in the state in which the optical system is focused on an object at a far distance and the other is the combined focal length of the object side positive lens and the cemented lens. When conditional expression (4) is satisfied, it is possible to accomplish downsizing of the optical system and favorable correction of aberrations.

When the value of f12e/f3' falls below the lower bound of conditional expression (4), the refractive power of the first lens unit cannot be sufficient. Then, it may be impossible for the optical system to have a wide angle of view, and the diameter of first lens unit is necessitated to be large. Otherwise a too large amount of aberrations will be generated by the object side positive lens and the cemented lens. Therefore, astigmatism, coma, and chromatic aberration of magnification will increase.

When the value of f12e/f3' exceeds the upper bound of conditional expression (4), the amount of aberrations generated by the first lens unit is too large. Then, coma and chromatic aberration will increase. Otherwise it is not possible to provide a sufficiently high refractive power with the object side positive lens and the cemented lens. Then, the optical system is necessitated to be large.

It is more preferred that the following conditional expression (4') be satisfied instead of conditional expression (4):

$$-0.59 < f12e/f3' < -0.43. \tag{4'}$$

It is more preferred that the following conditional expression (4") be satisfied instead of conditional expression (4):

$$-0.575 < f12e/f3' < -0.432. \tag{4''}$$

It is preferred that the endoscope objective optical system according to the embodiment satisfy the following conditional expression (5):

$$-50 < r2mf/fe < -2.5, \tag{5}$$

where r2mf is the radius of curvature of the object side surface of the positive meniscus lens, and fe is the focal length of the endoscope objective optical system in the state in which it is focused on an object at a far distance.

Conditional expression (5) relates to the shape of the object side surface of the positive meniscus lens. Satisfying conditional expression (5) allows favorable correction of spherical aberration and curvature of field.

When the value of r2mf/fe falls below the lower bound of conditional expression (5), the radius of curvature of the object side surface of the positive meniscus lens is too large. Then, the positive refractive power of the positive meniscus lens is large. Consequently, the image surface curves toward object side. For this reason, it is undesirable that the value of r2mf/fe falls below the lower bound of conditional expression (5).

When the value of r2mf/fe exceeds the upper bound of conditional expression (5), the radius of curvature of the object side surface of the positive meniscus lens is too small. This results in large spherical aberration. For this reason, it is undesirable that the value of r2mf/fe exceeds the upper bound of conditional expression (5).

It is more preferred that the following conditional expression (5') be satisfied instead of conditional expression (5):

$$-39 < r2mf/fe < -3. \tag{5'}$$

It is more preferred that the following conditional expression (5") be satisfied instead of conditional expression (5):

$$-37 < r2mf/fe < -3.1. \tag{5''}$$

It is preferred that the endoscope objective optical system according to the embodiment satisfy the following conditional expression (6):

$$0.01 < f3p/f3ce < 0.3, \tag{6}$$

where f3p is the focal length of the object side positive lens, and f3ce is the focal length of the cemented lens.

The positive refractive power of the object side positive lens contributes to image formation. It is necessary for the object side positive lens to have an appropriate positive refractive power in order to excellently form an image. Moreover, it is necessary for the object side positive lens and the cemented lens to favorably correct aberrations generated by the first lens unit and aberration generated in the second lens unit. To this end, it is preferred that the ratio of the focal length of the object side positive lens and the focal length of the cemented lens be set so that spherical aberration and coma can be favorably corrected while aiming at reduction in the entire length of the optical system and providing an appropriate back focus.

Conditional expression (6) limits the ratio of the focal length of the object side positive lens and the focal length of the cemented lens. Satisfying conditional expression (6) allows favorable correction of spherical aberration and coma. Then, excellent imaging performance is accomplished.

If the value of r2mf/fe falls below the lower bound of conditional expression (6), spherical aberration generated by the object side positive lens cannot be adequately corrected by the cemented lens.

If the value of r2mf/fe exceeds the upper bound of conditional expression (6), the entire length of the optical system is too long, or coma generated by the cemented lens cannot be adequately corrected by the object side positive lens.

It is more preferred that the following conditional expression (6') be satisfied instead of conditional expression (6):

$$0.06 < f3p/f3ce < 0.26. \tag{6'}$$

10

It is more preferred that the following conditional expression (6") be satisfied instead of conditional expression (6):

$$0.065 < f3p/f3ce < 0.25. \tag{6''}$$

It is preferred that the endoscope objective optical system according to the embodiment satisfy the following conditional expression (7):

$$0.5 < d3p/d3pce < 3, \tag{7}$$

where d3p is the thickness of the object side positive lens, and d3pce is the distance between the object side positive lens and the cemented lens.

Conditional expression (7) limits the ratio of the two surface distances, one of which is the thickness of the object side positive lens, and the other is the distance between the object side positive lens and the cemented lens. These two surface distances are distances on the optical axis. When conditional expression (7) is satisfied, it is possible to favorably correct aberrations while preventing an increase in the thickness of the object side positive lens.

The thickness of the object side positive lens influences the size of the object side positive lens. Therefore, conditional expression (7) relates to the size of the object side positive lens.

When the value of d3p/d3pce falls below the lower bound of conditional expression (7), the distance between the object side positive lens and the cemented lens is too large. This makes the entire length of the optical system long.

When the value of d3p/d3pce exceeds the upper bound of conditional expression (7), the thickness of the object side positive lens is too large. Then, the entire length of the optical system is necessitated be long. Moreover, it is difficult to provide a sufficient space between the object side positive lens and the cemented lens. Then, axial rays and off-axis rays are not separated sufficiently in the cemented lens, resulting in difficulty in correcting chromatic aberration of magnification and coma.

It is more preferred that the following conditional expression (7') be satisfied instead of conditional expression (7):

$$0.8 < d3p/d3pce < 2.5. \tag{7'}$$

It is more preferred that the following conditional expression (7") be satisfied instead of conditional expression (7):

$$0.85 < d3p/d3pce < 2.4. \tag{7''}$$

It is preferred that a specific group of lenses including the second lens unit, the object side positive lens, and the cemented lens in the endoscope objective optical system according to the embodiment satisfy the following conditional expression (8):

$$-3 < f23'k/f1 < -2, \tag{8}$$

where f23'k is the focal length of the specific group of lenses in the state in which the optical system is focused on an object at a near distance, and f1 is the focal length of the first lens unit.

Conditional expression (8) limits the ratio of the focal length of the specific group of lenses in the state in which the optical system is focused on an object at a near distance and the focal length of the first lens unit. The specific group of lenses includes the second lens unit, the object side positive lens, and the cemented lens. Satisfying conditional expression (8) allows favorable correction of aberrations.

When the value of f23'k/f1 falls below the lower bound of conditional expression (8), the refractive power of the first lens unit is too low. Then, the image surface curves greatly toward the object side.

When the value of f23'k/f1 exceeds the upper bound of conditional expression (8), the refractive power of the specific group of lenses is too low. Then, it is not possible for the specific group of lenses to make the Petzval sum of the first lens unit small. This results in large aberrations.

It is more preferred that the following conditional expression (8') be satisfied instead of conditional expression (8):

$$-2.65 < f23'k/f1 < -2. \qquad (8')$$

It is more preferred that the following conditional expression (8") be satisfied instead of conditional expression (8):

$$-2.61 < f23'k/f1 < -2.057. \qquad (8'')$$

It is preferred that the endoscope objective optical system according to the embodiment satisfy the following conditional expression (9):

$$0.38 < \Delta2/fe < 0.8, \qquad (9)$$

where $\Delta2$ is the amount of movement of the second lens unit, and fe is the focal length of the endoscope objective optical system in the state in which it is focused on an object at a far distance.

Conditional expression (9) relates to the amount of movement of the second lens unit. As described above, the second lens unit in the endoscope objective optical system according to the embodiment is moved. In order to accomplish downsizing and high imaging performance in optical systems including a moving lens unit, it is important to appropriately set the amount of movement of the moving lens unit. When conditional expression (9) is satisfied, it is possible to accomplish downsizing of the optical system and high imaging performance.

When the value of $\Delta2/fe$ falls below the lower bound of conditional expression (9), it is difficult to move the second lens unit by a sufficient amount of movement. Then, the displacement of the location of the image plane relative to the amount of movement of the lens unit becomes larger, resulting in deterioration in the imaging performance of the optical system. For this reason, it is undesirable that the value of $\Delta2/fe$ falls below the lower bound of conditional expression (9).

When the value of $\Delta2/fe$ exceeds the upper bound of conditional expression (9), the distance between the first lens unit and the second lens unit is too large. In this case, it is possible to move the second lens unit by a sufficient amount of movement. However, the entire length of the optical system is made large, and the size of the optical system is necessitated to be large.

It is more preferred that the following conditional expression (9') be satisfied instead of conditional expression (9):

$$0.38 < \Delta2/fe < 0.75. \qquad (9')$$

It is more preferred that the following conditional expression (9") be satisfied instead of conditional expression (9):

$$0.39 < \Delta2/fe < 0.7. \qquad (9'')$$

It is preferred that the endoscope objective optical system according to the embodiment satisfy the following conditional expression (10):

$$-18 < (r3pf - r3pr)/(r3pf + r3pr) < 40, \qquad (10)$$

where r3pf is the radius of curvature of the object side surface of the object side positive lens, and r3pr is the radius of curvature of the image side surface of the object side positive lens.

Conditional expression (10) relates to the shape of the object side positive lens. Satisfying conditional expression (10) can prevent or reduce increases in the spherical aberration and coma.

When the value of the term mentioned in conditional expression (10) falls below its lower bound, the radius of curvature of the object side surface of the object side positive lens is too large. Then, the positive refractive power of the object side positive lens is so small that the entire length of the optical system is necessitated to be large.

When the value of the term mentioned in conditional expression (10) exceeds its upper bound, the radius of curvature of the object side surface of the object side positive lens is too small. This results in increased spherical aberration and coma.

It is more preferred that the following conditional expression (10') be satisfied instead of conditional expression (10):

$$-12 < (r3pf - r3pr)/(r3pf + r3pr) < 37. \qquad (10')$$

It is more preferred that the following conditional expression (10") be satisfied instead of conditional expression (10):

$$-11.5 < (r3pf - r3pr)/(r3pf + r3pr) < 36. \qquad (10'')$$

It is preferred that the endoscope objective optical system according to the embodiment satisfy the following conditional expression (11):

$$-2.15 < (r3cpf - r3cpr)/(r3cpf + r3cpr) < -1, \qquad (11)$$

where r3cpf is the radius of curvature of the object side surface of the cemented lens, and r3cpr is the radius of curvature of the image side surface of the cemented lens.

Conditional expression (11) relates to the shape of the cemented lens. Satisfying conditional expression (11) allows favorable correction of coma and astigmatism.

As described above, the cemented lens is made up of a positive lens (which will be referred to as the "front positive lens" hereinafter) and a negative lens (which will be referred to as the "rear negative lens" hereinafter). The object side surface of the cemented lens is the object side surface of the front positive lens, and the image side surface of the cemented lens is the image side surface of the rear negative lens.

When the value of the term mentioned in conditional expression (11) falls below its lower bound, the radius of curvature of the object side surface of the front positive lens is too large, or the radius of curvature of the image side surface of the rear negative lens is too small. When the radius of curvature of the object side surface of the front positive lens is too large, the positive refractive power of the front positive lens is so low that the entire length of the optical system is necessitated to be long. When the radius of curvature of the image side surface of the rear negative lens is too small, coma and astigmatism will be corrected too much.

When the value of the term mentioned in conditional expression (11) exceeds its upper bound, the radius of curvature of the object side surface of the front positive lens is too small, or the radius of curvature of the image side surface of the rear negative lens is too large. When the radius of curvature of the object side surface of the front positive lens is too small, spherical aberration and coma will increase. When the radius of curvature of the image side surface of the rear negative lens is too large, coma and astigmatism will not be corrected sufficiently.

It is more preferred that the following conditional expression (11') be satisfied instead of conditional expression (11):

$$-2 < (r3cpf - r3cpr)/(r3cpf + r3cpr) < -1. \qquad (11')$$

It is more preferred that the following conditional expression (11") be satisfied instead of conditional expression (11):

$$-1.75 < (r3cpf - r3cpr)/(r3cpf + r3cpr) < -1. \qquad (11'')$$

It is preferred that the third lens unit in the endoscope objective optical system according to the embodiment include an image side positive lens provided on the image side of the cemented lens.

As described above, an imaging unit can be constructed using the endoscope objective optical system and an imager. In the case where the image side positive lens is provided on the image side of the cemented lens, in the process of assembling the imaging unit alignment of the image plane and the imaging surface of the imager is performed by moving (or changing the location of) the image side positive lens.

As the positive lens is provided, refraction by the positive refractive power occurs on the image side of the cemented lens. In this case, the amount of movement of the image plane relative to the amount of movement of the lens is smaller than in the case where the positive lens is not provided. Therefore, alignment of the image plane and the imaging surface of the imager can be carried out easily. As a result, it is possible to align the image plane with the imaging surface of the imager with high accuracy.

It is preferred that the aperture stop in the endoscope objective optical system according to the embodiment be located on the object side of the third lens unit.

When the aperture stop is located on the object side of the third lens unit, it is possible to make the difference between the F-number of the optical system in the state in which it is focused on an object at a far distance and that in the state in which it is focused on an object at a near distance small while maintaining high imaging performance.

The aperture stop may be disposed near the image side surface of the second lens unit, between the second lens unit and the third lens unit, or near the object side surface of the third lens unit. In the case where the aperture stop is disposed near the image side of the second lens unit, the aperture stop may be arranged to move with the second lens unit.

An endoscope according to the embodiment includes the endoscope objective optical system according to the embodiment.

The endoscope objective optical system according to the embodiment has sufficiently high imaging performance when focused regardless of the object distance, though it is small in size. Therefore, the endoscope according to the embodiment can produce clear images regardless of the object distance.

In the following, examples of the endoscope objective optical system will be described in detail with reference to the drawings. It should be understood that the present invention is not limited by the examples.

FIGS. 2A, 4A, 6A, 8A, 10A, 12A, and 14A are cross sectional views respectively showing the lenses in first to seventh examples of the endoscope objective optical system in the state in which they are focused on an object at a far distance. FIGS. 2B, 4B, 6B, 8B, 10B, 12B, and 14B are cross sectional views respectively showing the lenses in the first to seventh examples of the endoscope objective optical system in the state in which they are focused on an object at a near distance.

In the astigmatism graphs in the graphs showing aberrations of the examples, ΔM represents the aberration in meridional images, and ΔS represents the aberration in sagittal images.

FIGS. 3A, 5A, 7A, 9A, 11A, 13A, and 15A are graphs respectively showing spherical aberration (SA) in the first to seventh examples. FIGS. 3B, 5B, 7B, 9B, 11B, 13B, and 15B are graphs respectively showing astigmatism (AS) in the first to seventh examples. FIGS. 3C, 5C, 7C, 9C, 11C, 13C, and 15C are graphs respectively showing distortion (DT) in the first to seventh examples. FIGS. 3D, 5D, 7D, 9D, 11D, 13D, and 15D are graphs respectively showing chromatic aberration of magnification (CC) in the first to seventh examples. All these graphs show aberrations in the state in which the optical systems are focused on an object at a far distance.

FIGS. 3E, 5E, 7E, 9E, 11E, 13E, and 15E are graphs respectively showing spherical aberration (SA) in the first to seventh examples. FIGS. 3F, 5F, 7F, 9F, 11F, 13F, and 15F are graphs respectively showing astigmatism (AS) in the first to seventh examples. FIGS. 3G, 5G, 7G, 9G, 11G, 13G, and 15G are graphs respectively showing distortion (DT) in the first to seventh examples. FIGS. 3H, 5H, 7H, 9H, 11H, 13H, and 15H are graphs respectively showing chromatic aberration of magnification (CC) in the first to seventh examples. All these graphs show aberrations in the state in which the optical systems are focused on an object at a near distance.

Figure 2A:
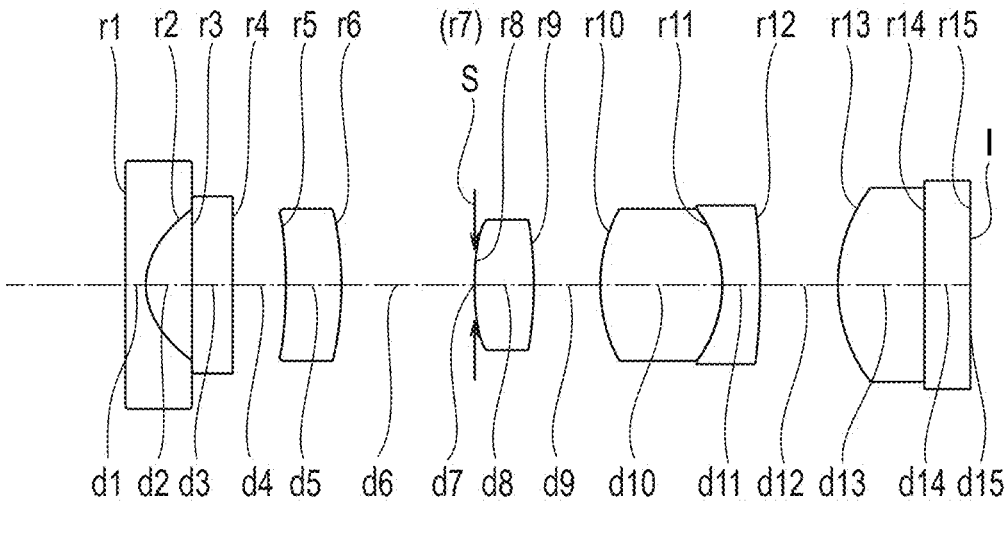
FIGS. 2A and 2B are cross sectional views of a first example of the endoscope objective optical system.
Figure 2B:
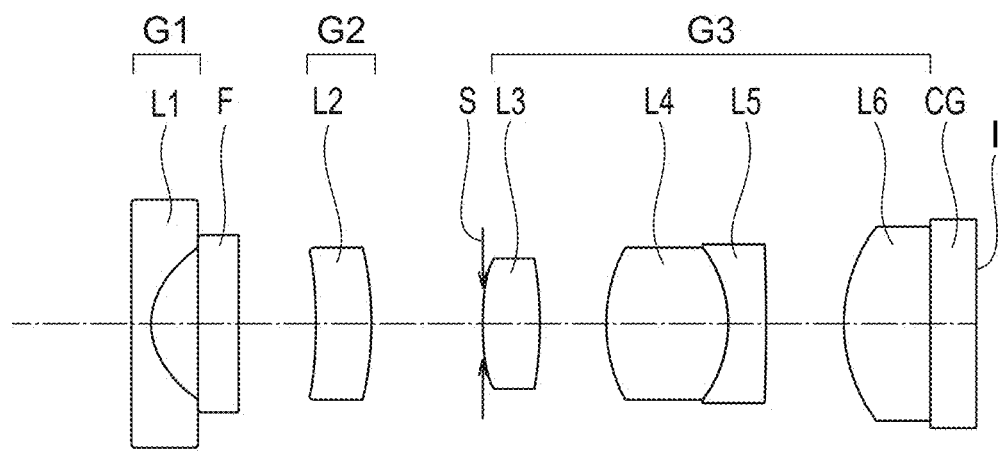
Figures 3A, 3B, 3C, 3D:
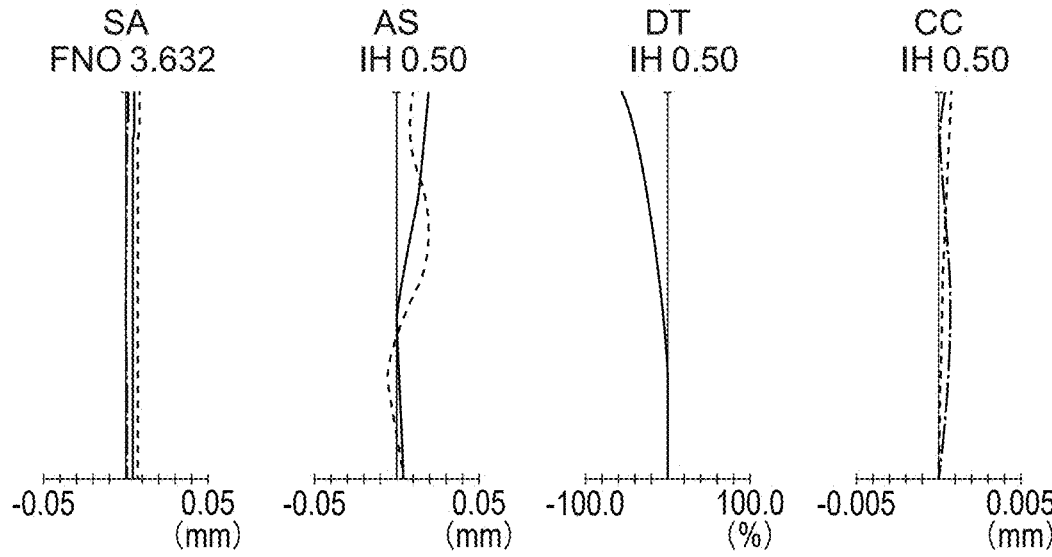
FIGS. 3A, 3B, 3C, 3D, 3E, 3F, 3G, and 3H are aberration graphs of the first example of the endoscope objective optical system.
Figures 3E, 3F, 3G, 3H:
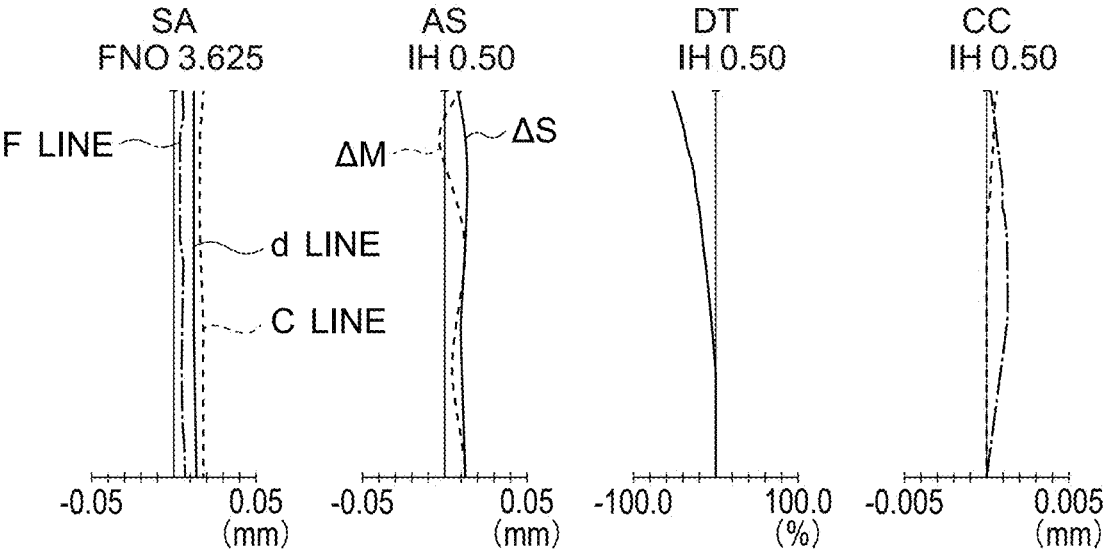

FIGS. 2A and 2B are cross sectional views of the lenses in the first example of the endoscope objective optical system. FIGS. 3A, 3B, 3C, 3D, 3E, 3F, 3G, and 3H are aberration graphs of the first example of the endoscope objective optical system.

The first example of the endoscope objective optical system includes, in order from the object side, a first lens unit G1 having a negative refractive power, a second lens unit G2 having a positive refractive power, and a third lens unit G3 having a positive refractive power.

The first lens unit G1 includes a plano-concave negative lens L1 having a flat surface facing the object side.

The second lens unit G2 includes a positive meniscus lens L2 having a convex surface facing the image side.

The third lens unit G3 includes a biconvex positive lens L3, a biconvex positive lens L4, a negative meniscus lens L5 having a convex surface facing the image side, and a plano-convex positive lens L6 having a flat surface facing the image side. The biconvex positive lens L4 and the negative meniscus lens L5 are cemented together to constitute a cemented lens.

The first example of the endoscope objective optical system further includes an aperture stop S disposed between the second lens unit G2 and the third lens unit G3. More specifically, the aperture stop S is located at the vertex of the object side surface of the biconvex positive lens L3.

The first example of the endoscope objective optical system further includes a plane parallel plate F disposed between the first lens unit G1 and the second lens unit G2. For example, the plane parallel plate F is an optical filter. The first example of the endoscope objective optical system also includes a cover glass CG disposed on the image side of the third lens unit G3. The cover glass CG is cemented to the plano-convex positive lens L6.

During focusing, the second lens unit G2 is moved. When focusing is changed from far distance object to near distance object, the second lens unit G2 moves toward the image side.

Figure 4A:
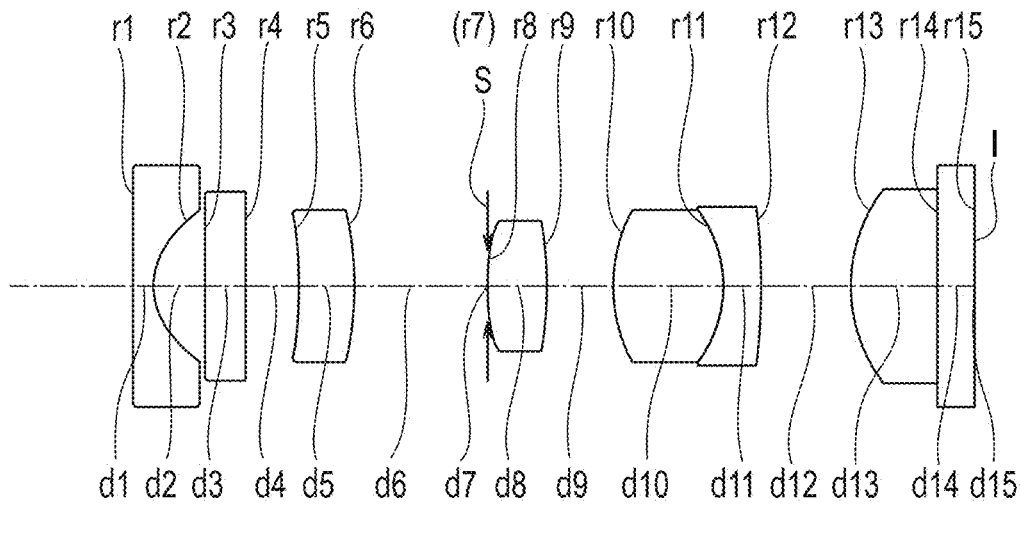
FIGS. 4A and 4B are cross sectional views of a second example of the endoscope objective optical system.
Figure 4B:
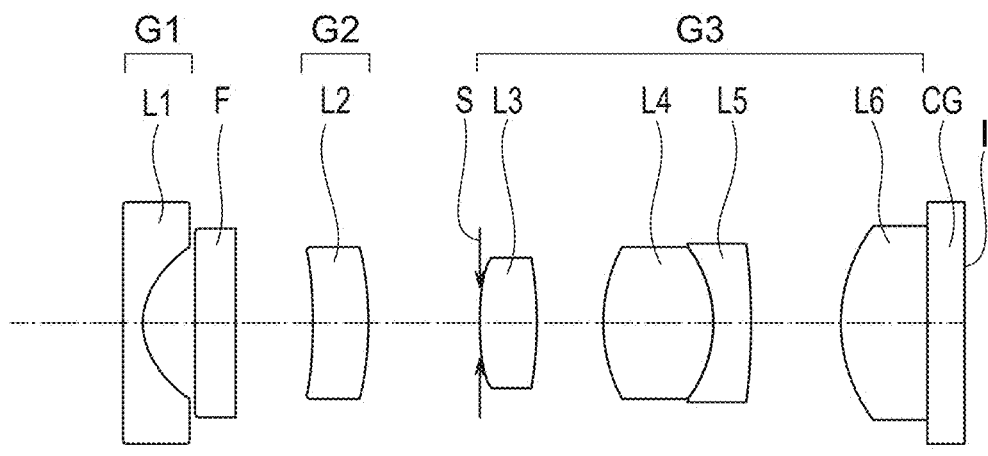
Figures 5A, 5B, 5C, 5D:
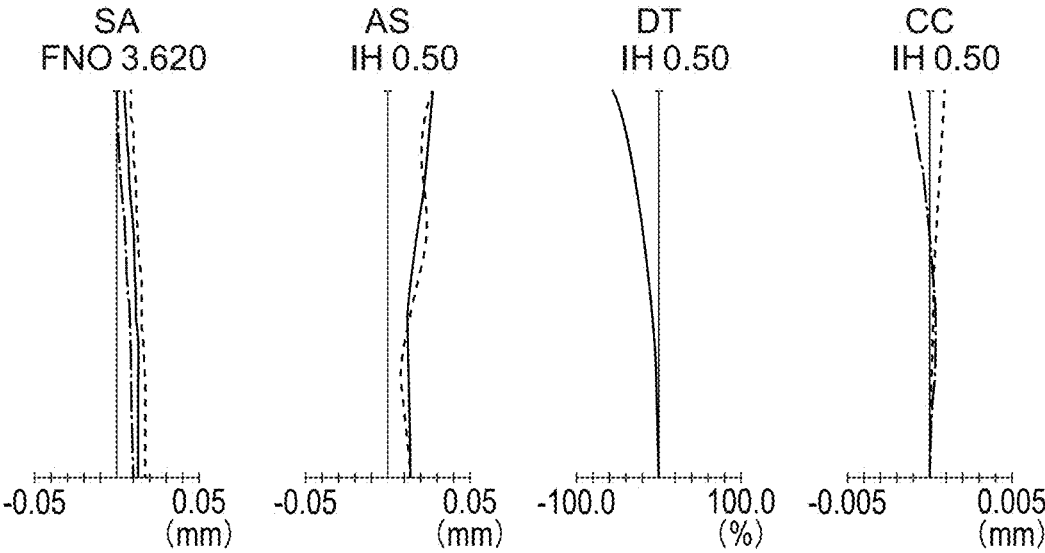
FIGS. 5A, 5B, 5C, 5D, 5E, 5F, 5G, and 5H are aberration graphs of the second example of the endoscope objective optical system.
Figures 5E, 5F, 5G, 5H:
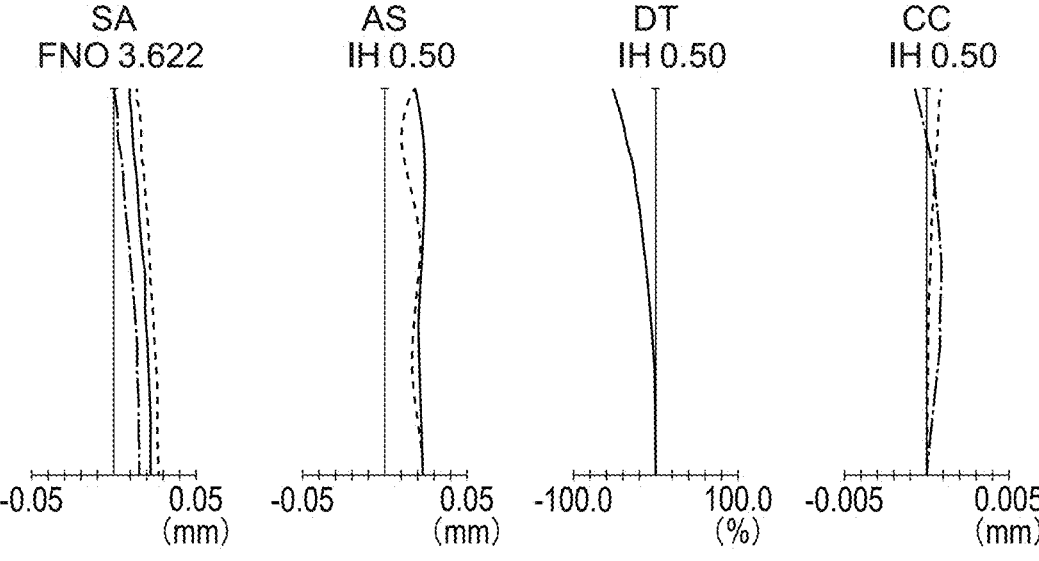

FIGS. 4A and 4B are cross sectional views of the lenses in the second example of the endoscope objective optical system. FIGS. 5A, 5B, 5C, 5D, 5E, 5F, 5G, and 5H are aberration graphs of the second example of the endoscope objective optical system.

The second example of the endoscope objective optical system includes, in order from the object side, a first lens unit G1 having a negative refractive power, a second lens unit G2 having a positive refractive power, and a third lens unit G3 having a positive refractive power.

The first lens unit G1 includes a plano-concave negative lens L1 having a flat surface facing the object side.

The second lens unit G2 includes a positive meniscus lens L2 having a convex surface facing the image side.

The third lens unit G3 includes a biconvex positive lens L3, a biconvex positive lens L4, a negative meniscus lens L5 having a convex surface facing the image side, and a plano-convex positive lens L6 having a flat surface facing the image side. The biconvex positive lens L4 and the negative meniscus lens L5 are cemented together to constitute a cemented lens.

The second example of the endoscope objective optical system further includes an aperture stop S disposed between the second lens unit G2 and the third lens unit G3. More specifically, the aperture stop S is located at the vertex of the object side surface of the biconvex positive lens L3.

The second example of the endoscope objective optical system further includes a plane parallel plate F disposed between the first lens unit G1 and the second lens unit G2. For example, the plane parallel plate F is an optical filter. The second example of the endoscope objective optical system also includes a cover glass CG disposed on the image side of the third lens unit G3. The cover glass CG is cemented to the plano-convex positive lens L6.

During focusing, the second lens unit G2 is moved. When focusing is changed from far distance object to near distance object, the second lens unit G2 moves toward the image side.

Figure 6A:
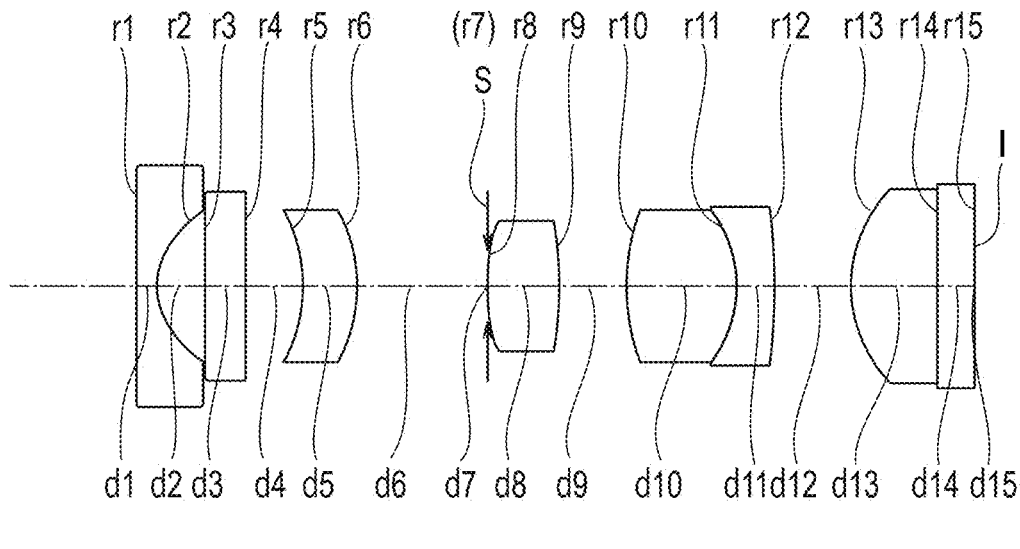
FIGS. 6A and 6B are cross sectional views of a third example of the endoscope objective optical system.
Figure 6B:
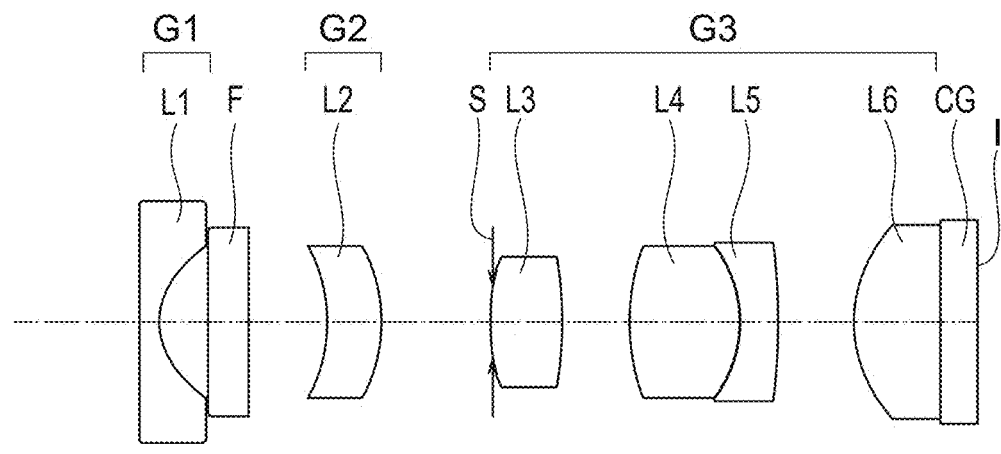
Figures 7A, 7B, 7C, 7D:
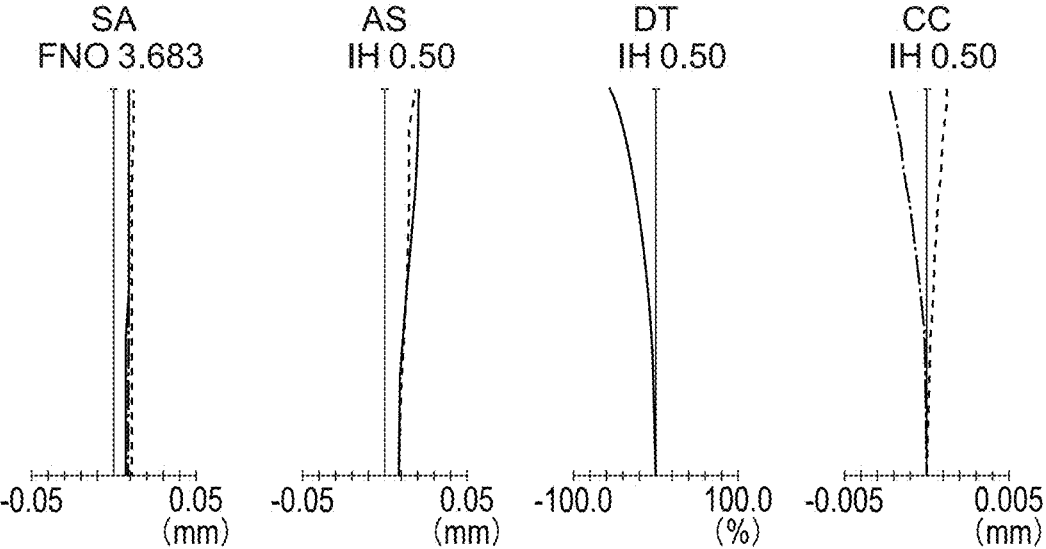
FIGS. 7A, 7B, 7C, 7D, 7E, 7F, 7G, and 7H are aberration graphs of the third example of the endoscope objective optical system.
Figures 7E, 7F, 7G, 7H:
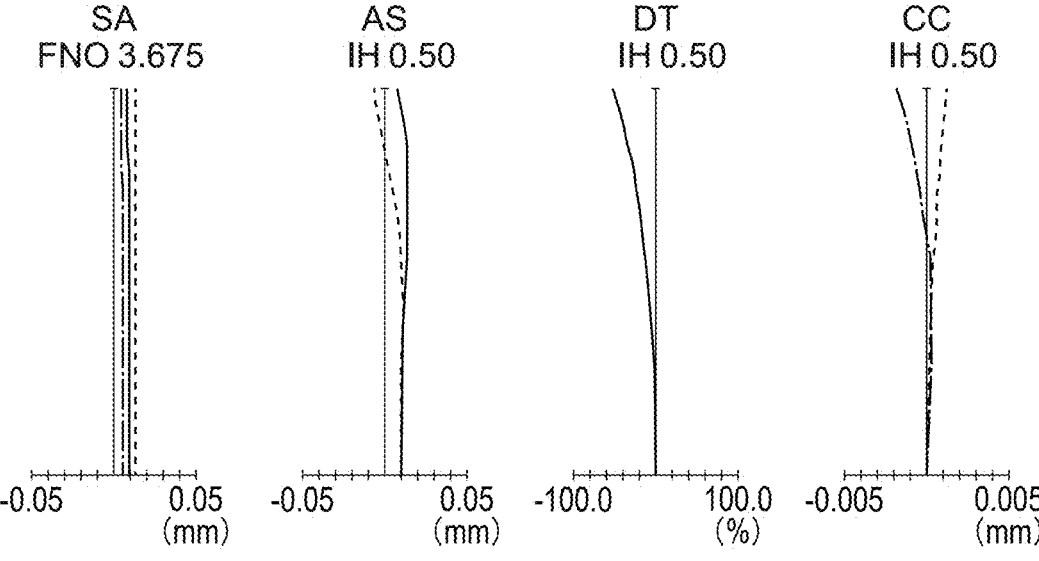

FIGS. 6A and 6B are cross sectional views of the lenses in the third example of the endoscope objective optical system. FIGS. 7A, 7B, 7C, 7D, 7E, 7F, 7G, and 7H are aberration graphs of the third example of the endoscope objective optical system.

The third example of the endoscope objective optical system includes, in order from the object side, a first lens unit G1 having a negative refractive power, a second lens unit G2 having a positive refractive power, and a third lens unit G3 having a positive refractive power.

The first lens unit G1 includes a plano-concave negative lens L1 having a flat surface facing the object side.

The second lens unit G2 includes a positive meniscus lens L2 having a convex surface facing the image side.

The third lens unit G3 includes a biconvex positive lens L3, a biconvex positive lens L4, a plano-concave lens L5 having a flat surface facing the image side, and a plano-convex positive lens L6 having a flat surface facing the image side. The biconvex positive lens L4 and the plano-concave lens L5 are cemented together to constitute a cemented lens.

The third example of the endoscope objective optical system further includes an aperture stop S disposed between the second lens unit G2 and the third lens unit G3. More specifically, the aperture stop S is located at the vertex of the object side surface of the biconvex positive lens L3.

The third example of the endoscope objective optical system further includes a plane parallel plate F disposed between the first lens unit G1 and the second lens unit G2. For example, the plane parallel plate F is an optical filter. The third example of the endoscope objective optical system also includes a cover glass CG disposed on the image side of the third lens unit G3. The cover glass CG is cemented to the plano-convex positive lens L6.

During focusing, the second lens unit G2 is moved. When focusing is changed from far distance object to near distance object, the second lens unit G2 moves toward the image side.

Figure 8A:
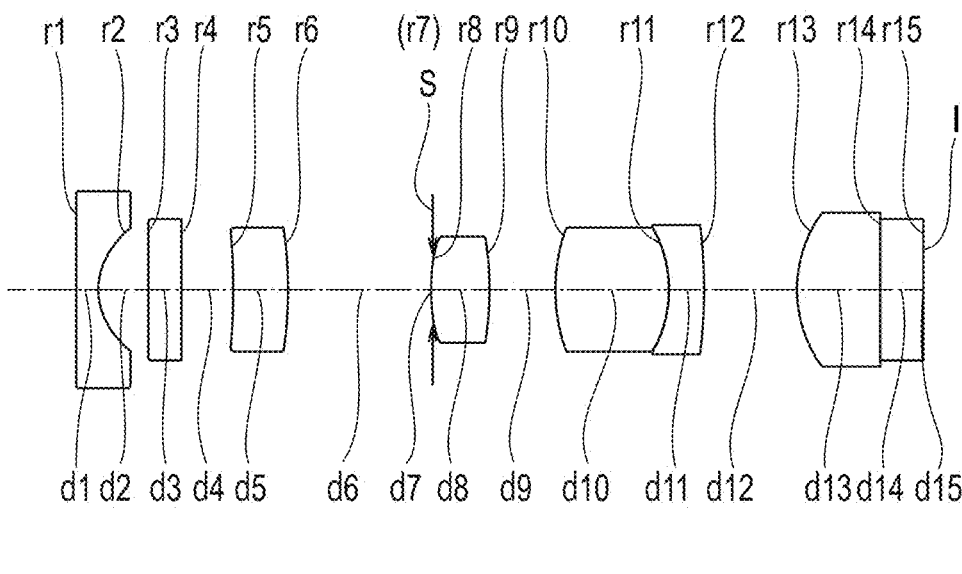
FIGS. 8A and 8B are cross sectional views of a fourth example of the endoscope objective optical system.
Figure 8B:
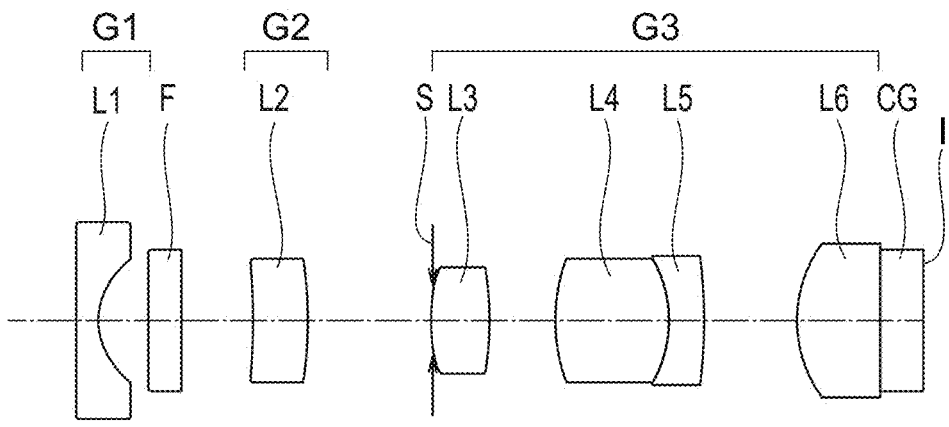
Figures 9A, 9B, 9C, 9D:
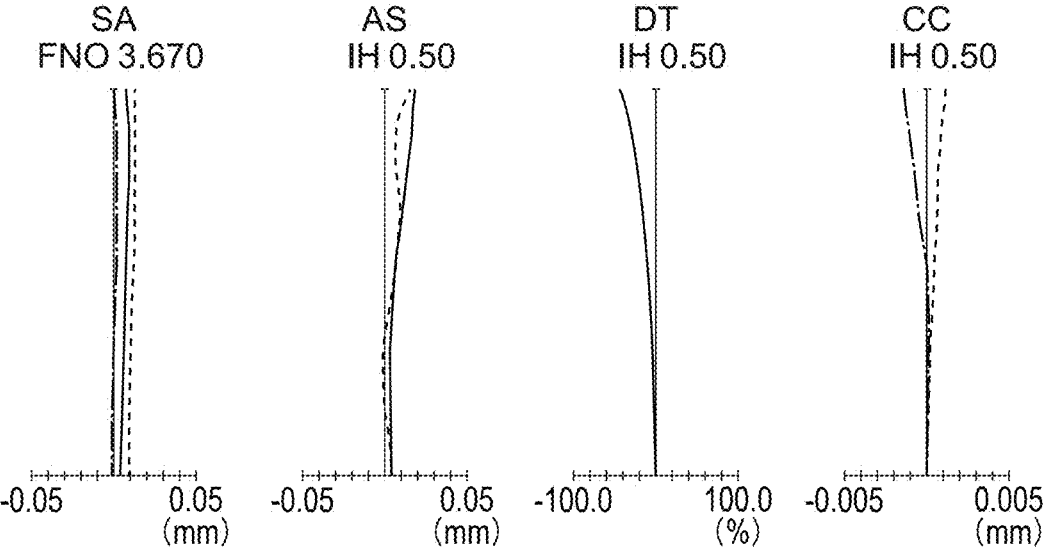
FIGS. 9A, 9B, 9C, 9D, 9E, 9F, 9G, and 9H are aberration graphs of the fourth example of the endoscope objective optical system.
Figures 9E, 9F, 9G, 9H:
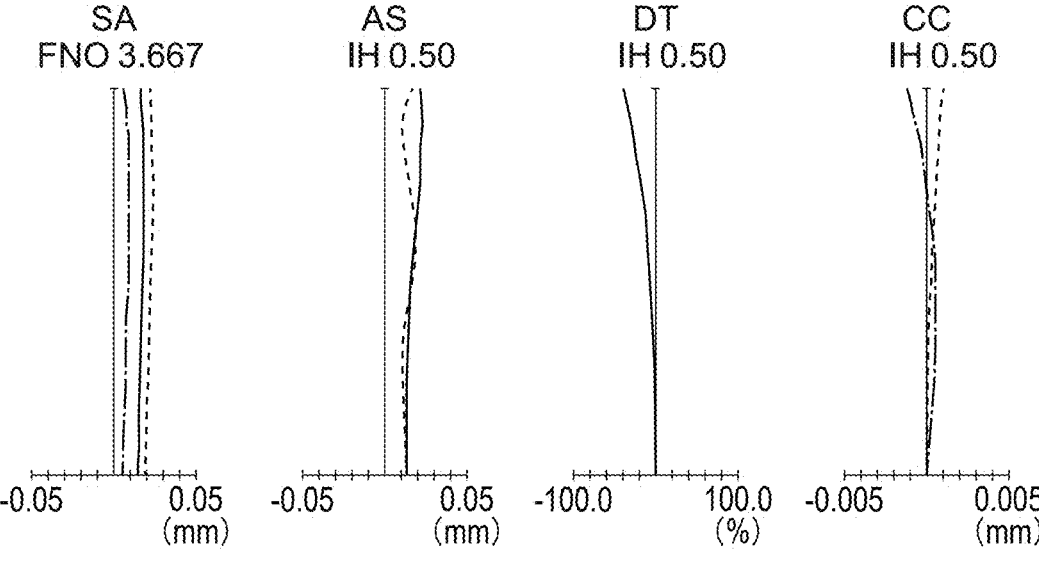

FIGS. 8A and 8B are cross sectional views of the lenses in the fourth example of the endoscope objective optical system. FIGS. 9A, 9B, 9C, 9D, 9E, 9F, 9G, and 9H are aberration graphs of the fourth example of the endoscope objective optical system.

The fourth example of the endoscope objective optical system includes, in order from the object side, a first lens unit G1 having a negative refractive power, a second lens unit G2 having a positive refractive power, and a third lens unit G3 having a positive refractive power.

The first lens unit G1 includes a plano-concave negative lens L1 having a flat surface facing the object side.

The second lens unit G2 includes a positive meniscus lens L2 having a convex surface facing the image side.

The third lens unit G3 includes a biconvex positive lens L3, a biconvex positive lens L4, a negative meniscus lens L5 having a convex surface facing the image side, and a plano-convex positive lens L6 having a flat surface facing the image side. The biconvex positive lens L4 and the negative meniscus lens L5 are cemented together to constitute a cemented lens.

The fourth example of the endoscope objective optical system further includes an aperture stop S disposed between the second lens unit G2 and the third lens unit G3. More specifically, the aperture stop S is located at the vertex of the object side surface of the biconvex positive lens L3.

The fourth example of the endoscope objective optical system further includes a plane parallel plate F disposed between the first lens unit G1 and the second lens unit G2. For example, the plane parallel plate F is an optical filter. The fourth example of the endoscope objective optical system also includes a cover glass CG disposed on the image side of the third lens unit G3. The cover glass CG is cemented to the plano-convex positive lens L6.

During focusing, the second lens unit G2 is moved. When focusing is changed from far distance object to near distance object, the second lens unit G2 moves toward the image side.

Figure 10A:
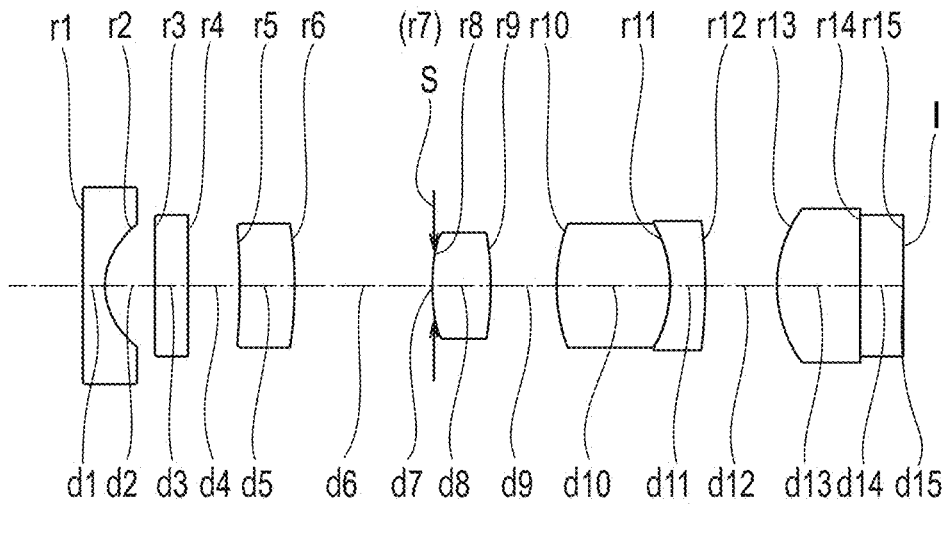
FIGS. 10A and 10B are cross sectional views of a fifth example of the endoscope objective optical system.
Figure 10B:
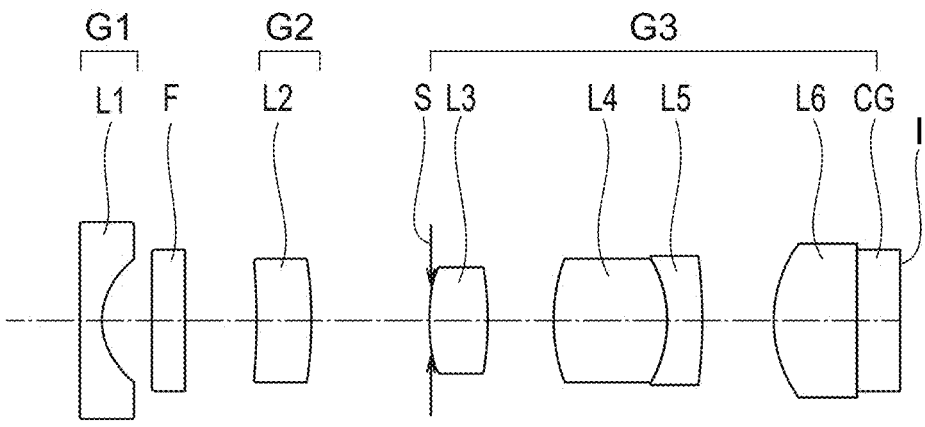
Figures 11A, 11B, 11C, 11D:
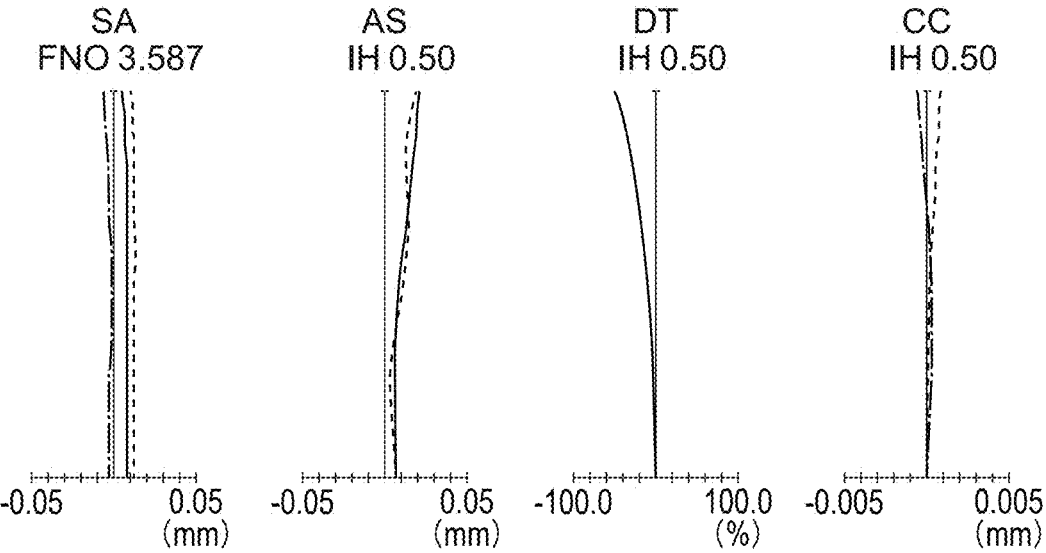
FIGS. 11A, 11B, 11C, 11D, 11E, 11F, 11G, and 11H are aberration graphs of the fifth example of the endoscope objective optical system.
Figures 11E, 11F, 11G, 11H:
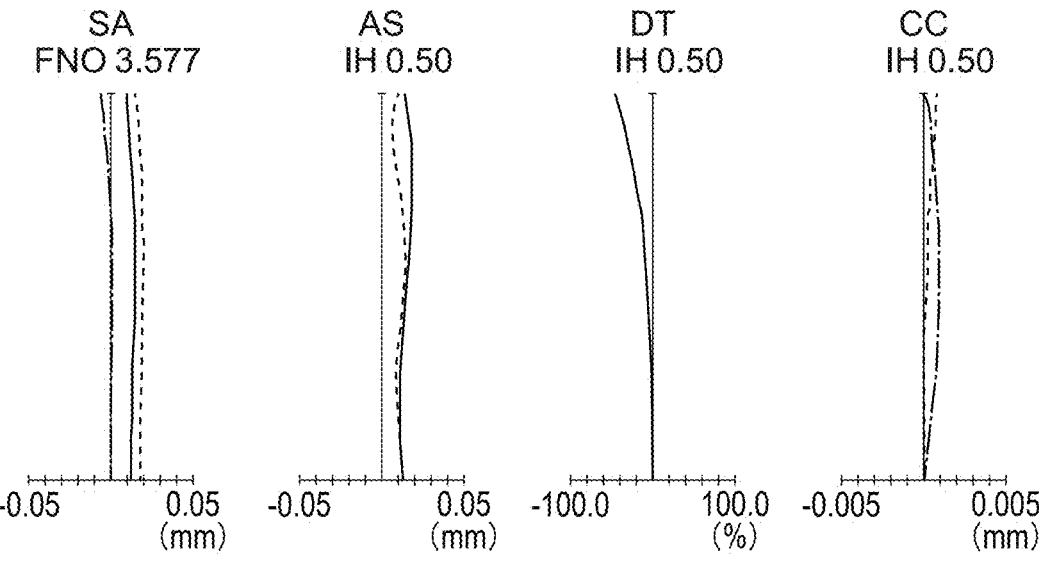

FIGS. 10A and 10B are cross sectional views of the lenses in the fifth example of the endoscope objective optical system. FIGS. 11A, 11B, 11C, 11D, 11E, 11F, 11G, and 11H are aberration graphs of the fifth example of the endoscope objective optical system.

The fifth example of the endoscope objective optical system includes, in order from the object side, a first lens unit G1 having a negative refractive power, a second lens unit G2 having a positive refractive power, and a third lens unit G3 having a positive refractive power.

The first lens unit G1 includes a plano-concave negative lens L1 having a flat surface facing the object side.

The second lens unit G2 includes a positive meniscus lens L2 having a convex surface facing the image side.

The third lens unit G3 includes a biconvex positive lens L3, a biconvex positive lens L4, a negative meniscus lens L5 having a convex surface facing the image side, and a plano-convex positive lens L6 having a flat surface facing the image side. The biconvex positive lens L4 and the negative meniscus lens L5 are cemented together to constitute a cemented lens.

The fifth example of the endoscope objective optical system further includes an aperture stop S disposed between the second lens unit G2 and the third lens unit G3. More specifically, the aperture stop S is located at the vertex of the object side surface of the biconvex positive lens L3.

The fifth example of the endoscope objective optical system further includes a plane parallel plate F disposed between the first lens unit G1 and the second lens unit G2. For example, the plane parallel plate F is an optical filter. The fifth example of the endoscope objective optical system also includes a cover glass CG disposed on the image side of the third lens unit G3. The cover glass CG is cemented to the plano-convex positive lens L6.

During focusing, the second lens unit G2 is moved. When focusing is changed from far distance object to near distance object, the second lens unit G2 moves toward the image side.

Figure 12A:
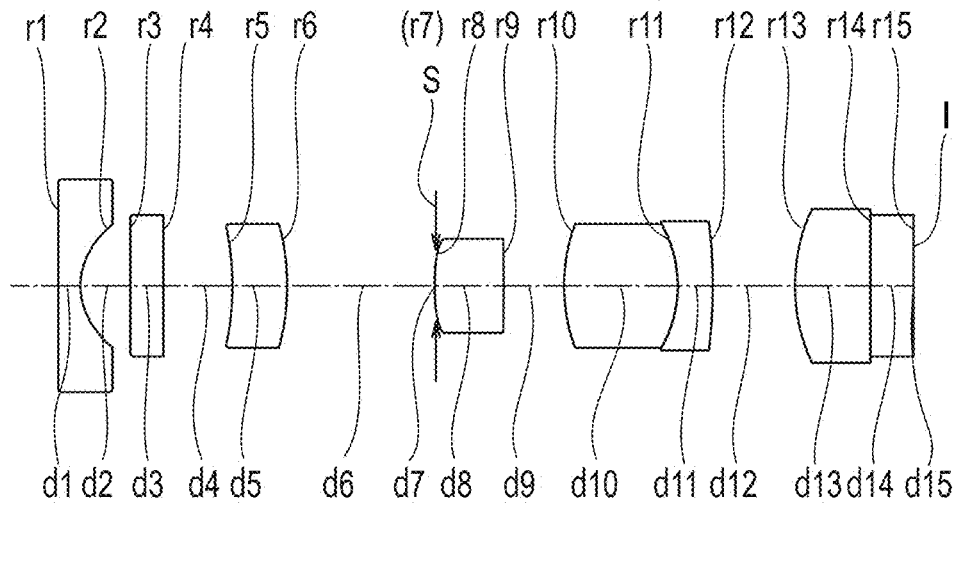
FIGS. 12A and 12B are cross sectional views of a sixth example of the endoscope objective optical system.
Figure 12B:
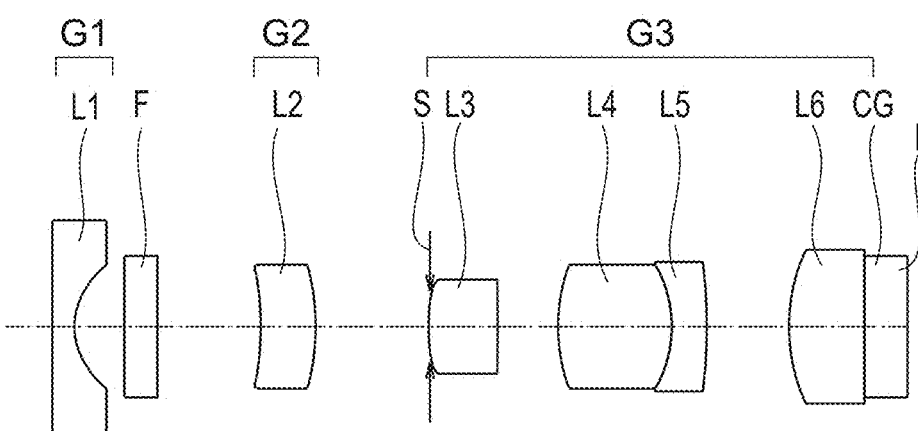
Figures 13A, 13B, 13C, 13D:
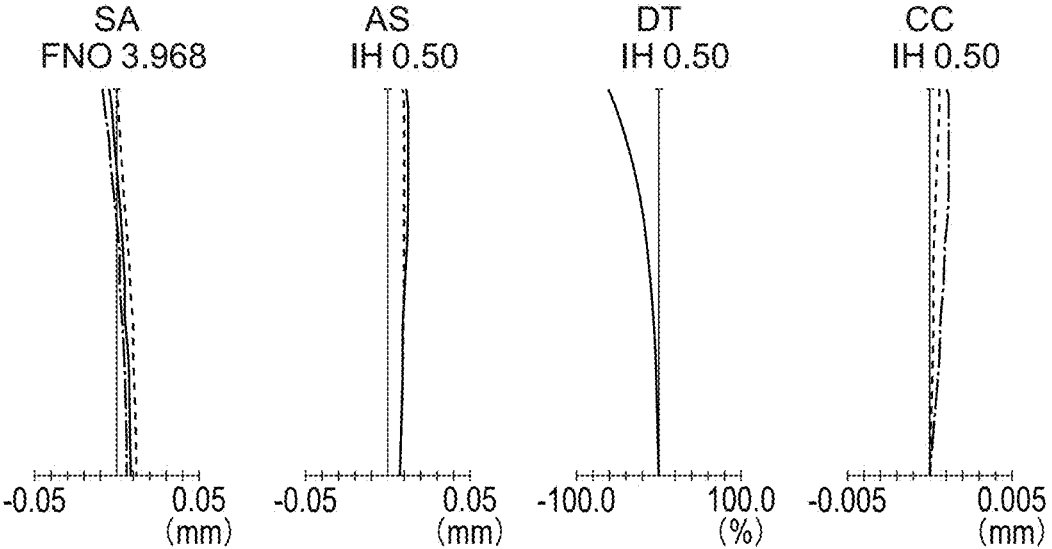
FIGS. 13A, 13B, 13C, 13D, 13E, 13F, 13G, and 13H are aberration graphs of the sixth example of the endoscope objective optical system.
Figures 13E, 13F, 13G, 13H:
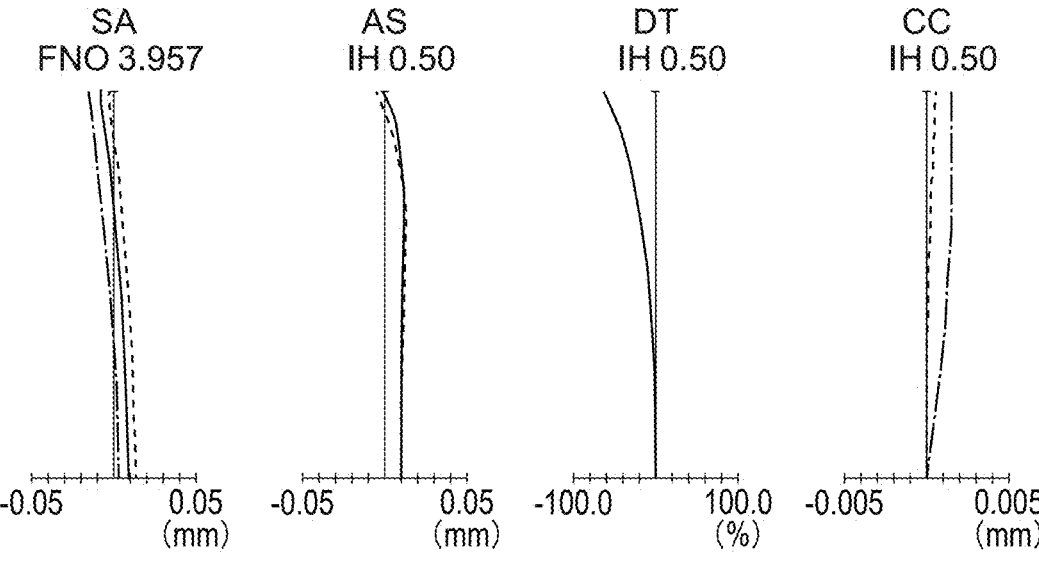

FIGS. 12A and 12B are cross sectional views of the lenses in the sixth example of the endoscope objective optical system. FIGS. 13A, 13B, 13C, 13D, 13E, 13F, 13G, and 13H are aberration graphs of the sixth example of the endoscope objective optical system.

The sixth example of the endoscope objective optical system includes, in order from the object side, a first lens unit G1 having a negative refractive power, a second lens unit G2 having a positive refractive power, and a third lens unit G3 having a positive refractive power.

The first lens unit G1 includes a plano-concave negative lens L1 having a flat surface facing the object side.

The second lens unit G2 includes a positive meniscus lens L2 having a convex surface facing the image side.

The third lens unit G3 includes a biconvex positive lens L3, a biconvex positive lens L4, a plano-concave negative lens L5 having a flat surface facing the image side, and a plano-convex positive lens L6 having a flat surface facing the image side. The biconvex positive lens L4 and the plano-concave negative lens L5 are cemented together to constitute a cemented lens.

The fifth example of the endoscope objective optical system further includes an aperture stop S disposed between the second lens unit G2 and the third lens unit G3. More specifically, the aperture stop S is located at the vertex of the object side surface of the biconvex positive lens L3.

The fifth example of the endoscope objective optical system further includes a plane parallel plate F disposed between the first lens unit G1 and the second lens unit G2. For example, the plane parallel plate F is an optical filter. The fifth example of the endoscope objective optical system also includes a cover glass CG disposed on the image side of the third lens unit G3. The cover glass is cemented to the plano-convex positive lens L6.

During focusing, the second lens unit G2 is moved. When focusing is changed from far distance object to near distance object, the second lens unit G2 moves toward the image side.

Figure 14A:
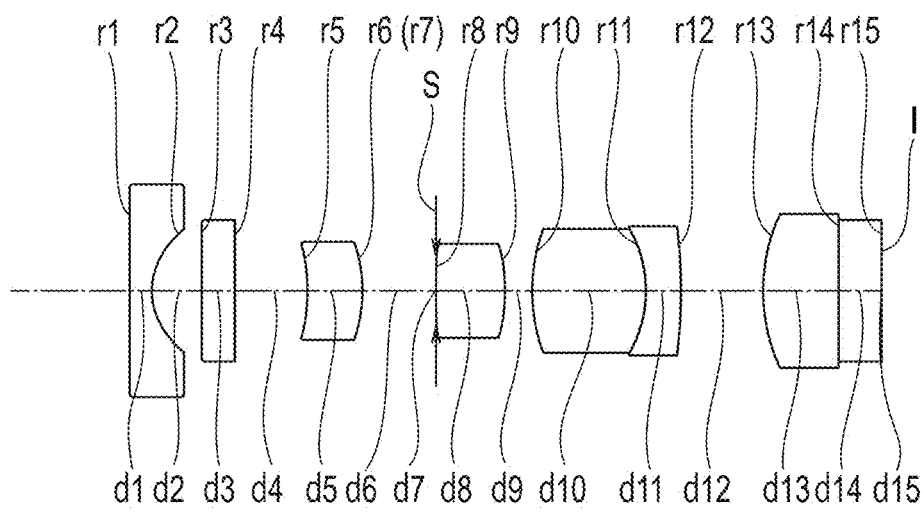
FIGS. 14A and 14B are cross sectional views of a seventh example of the endoscope objective optical system.
Figure 14B:
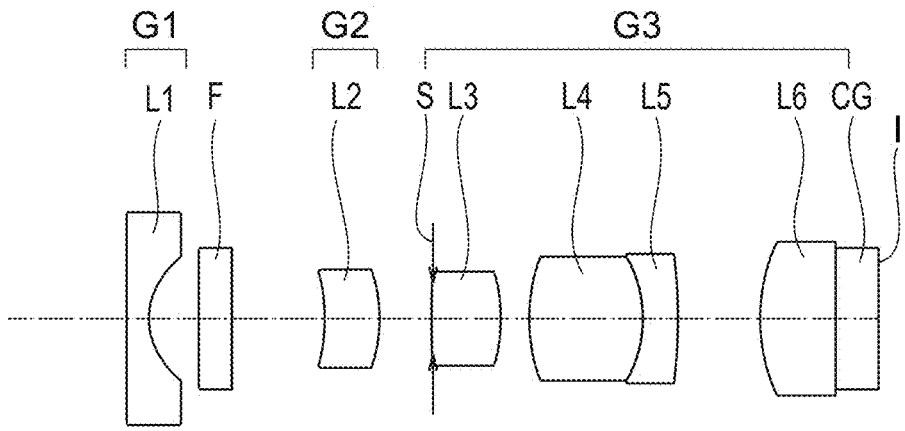
Figures 15A, 15B, 15C, 15D:
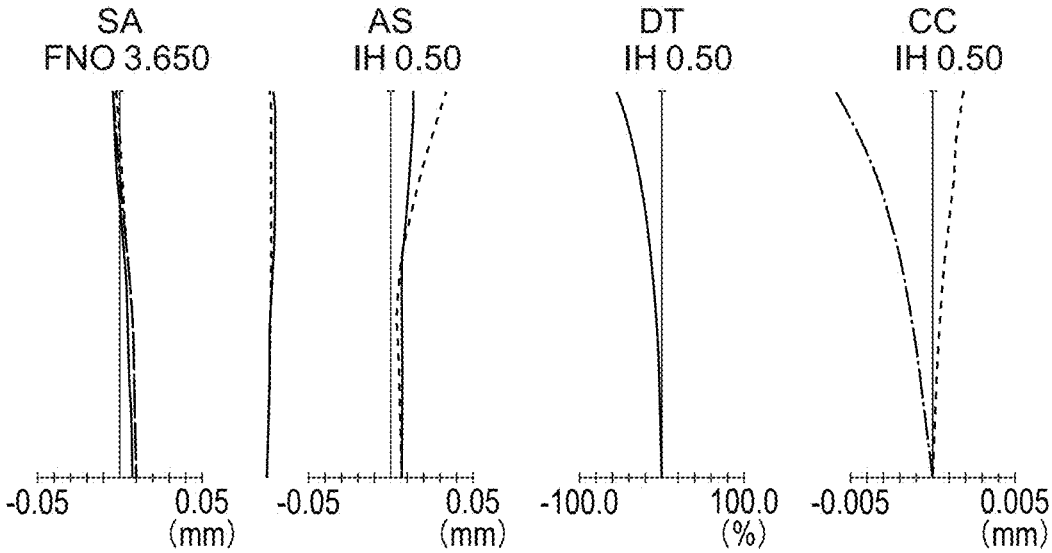
FIGS. 15A, 15B, 15C, 15D, 15E, 15F, 15G, and 15H are aberration graphs of the seventh example of the endoscope objective optical system.
Figures 15E, 15F, 15G, 15H:
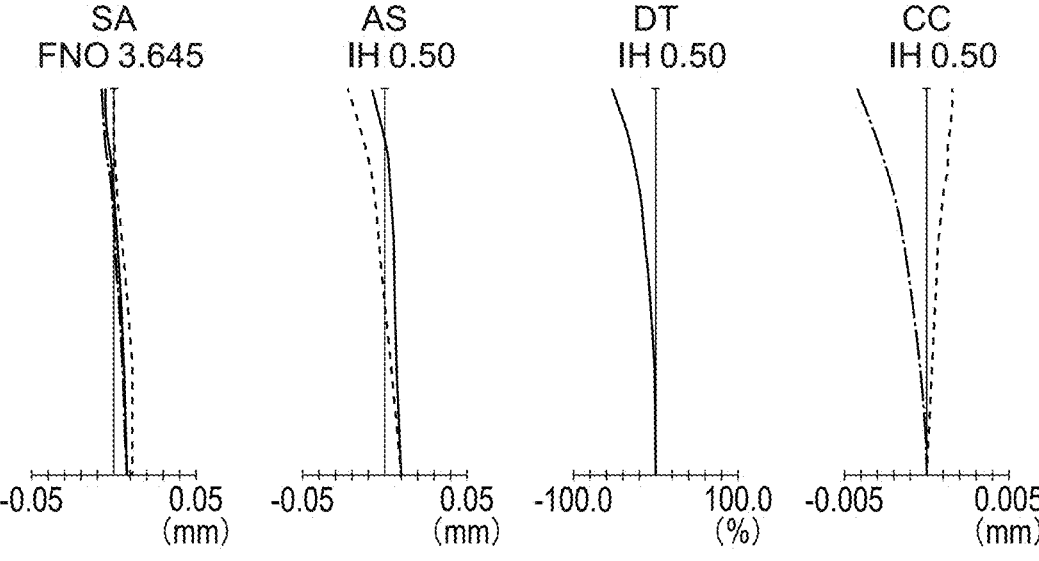

FIGS. 14A and 14B are cross sectional views of the lenses in the seventh example of the endoscope objective optical system. FIGS. 15A, 15B, 15C, 15D, 15E, 15F, 15G, and 15H are aberration graphs of the seventh example of the endoscope objective optical system.

The seventh example of the endoscope objective optical system includes, in order from the object side, a first lens unit G1 having a negative refractive power, a second lens unit G2 having a positive refractive power, and a third lens unit G3 having a positive refractive power. The first lens unit G1 includes a plano-concave negative lens L1 having a flat surface facing the object side.

The second lens unit G2 includes a positive meniscus lens L2 having a convex surface facing the image side.

The third lens unit G3 includes a biconvex positive lens L3, a biconvex positive lens L4, a negative meniscus lens L5 having a convex surface facing the image side, and a plano-convex positive lens L6 having a flat surface facing the image side. The biconvex positive lens L4 and the negative meniscus lens L5 are cemented together to constitute a cemented lens.

The seventh example of the endoscope objective optical system further includes an aperture stop S disposed between the second lens unit G2 and the third lens unit G3. More specifically, the aperture stop S is located at the vertex of the object side surface of the biconvex positive lens L3.

The seventh example of the endoscope objective optical system further includes a plane parallel plate F disposed between the first lens unit G1 and the second lens unit G2. For example, the plane parallel plate F is an optical filter. The seventh example of the endoscope objective optical system also includes a cover glass CG disposed on the image side of the third lens unit G3. The cover glass CG is cemented to the plano-convex positive lens L6.

During focusing, the second lens unit G2 is moved. When focusing is changed from far distance object to near distance object, the second lens unit G2 moves toward the image side.

Numerical data of the above examples is given below. In the surface data, r is the radius of curvature of each lens surface, d is the distance between adjacent lenses, nd is the refractive index of each lens for the d-line, and vd is the Abbe number of each lens. The stop mentioned in the surface data is the aperture stop. The asterisk (*) suffixed to some surface numbers indicates that those surfaces are aspherical surfaces.

In the various data, f is the focal length for the e-line, Fno is the F number, OBJ is the object distance, and ω is the angle of view. In the focal length data, f1, f2, and f3 are focal lengths of the respective lens units. The captions "Far" and "Near" respectively mean the state in which the optical system is focused on an object at a far distance and the state in which the optical system is focused on an object at a near distance.

The aspherical surface shape is expressed by the following equation in a coordinate system having the Z axis taken along the optical axis and the Y axis taken along a direction perpendicular to the optical axis:

$$z = (y^2/r)/\left[1 + \{1 - (1+k)(y/r)^2\}^{1/2}\right] +$$
$$A4y^4 + A6y^6 + A8y^8 + A10y^{10} + A12y^{12} + \dots ,$$

where k is the constant of the cone, and A4, A6, A8, A10, A12 . . . are aspheric coefficients.

The notation "e-n" used in the numerical data of the aspheric coefficients stands for "$10^n$" (n-th power of 10).

The above sings and notations are commonly used in the numerical data of other examples that will be described later.

Numerical Example 1

| Unit mm | | | | |
| --- | --- | --- | --- | --- |
| Surface data | | | | |
| Surface no. | r | d | nd | vd |
| 1 | ∞ | 0.15 | 1.88300 | 40.76 |
| 2* | 0.547 | 0.42 | | |
| 3 | ∞ | 0.30 | 1.49400 | 75.01 |
| 4 | ∞ | variable | | |
| 5* | −3.369 | 0.45 | 1.80610 | 40.92 |
| 6* | −2.759 | variable | | |
| 7(stop) | ∞ | 0.00 | | |
| 8 | 3.101 | 0.48 | 1.83400 | 37.16 |
| 9 | −4.392 | 0.56 | | |
| 10 | 1.231 | 1.02 | 1.43875 | 94.66 |
| 11 | −0.945 | 0.29 | 1.95906 | 17.47 |
| 12 | −4.660 | 0.66 | | |
| 13 | 1.308 | 0.70 | 1.51633 | 64.14 |
| 14 | ∞ | 0.35 | 1.50510 | 63.26 |
| 15 | ∞ | 0 | | |
| Image plane | ∞ | | | |

Aspheric surface data

2nd surface
k = −4.606
A4 = 2.48215e+00, A6 = −5.51638e+00, A8 = 7.15361e+00
5th surface
k = 0.000
A4 = −1.38015e−01, A6 = −1.14714e+00, A8 = 7.89531e+00,
A10 = −1.77941e+01, A12 = 1.55376e+01
6th surface
k = 0.000
A4 = −9.42551e−02, A6 = −2.36266e−01, A8 = 8.68609e−01

-continued

| Unit mm | | |
| --- | --- | --- |
| Various data | | |
| | far distance | near distance |
| f | 0.48 | 0.47 |
| Fno | 3.63 | 3.62 |
| OBJ | 13.0 | 2.7 |
| Angle of view 2ω | 133.86 | 135.82 |
| d4 | 0.47 | 0.67 |
| d6 | 1.15 | 0.95 |

| Focal length of each unit | | |
| --- | --- | --- |
| f1 = −0.62 | f2 = 14.22 | f3 = 2.04 |

| Unit mm | | | | |
| --- | --- | --- | --- | --- |
| Surface data | | | | |
| Surface no. | r | d | nd | vd |
| 1 | ∞ | 0.20 | 1.88300 | 40.76 |
| 2* | 0.525 | 0.42 | | |
| 3 | ∞ | 0.30 | 1.49400 | 75.01 |
| 4 | ∞ | variable | | |
| 5* | −7.317 | 0.45 | 1.80625 | 40.91 |
| 6* | −4.421 | variable | | |
| 7(stop) | ∞ | 0.00 | | |
| 8 | 3.105 | 0.50 | 1.83400 | 37.16 |
| 9 | −3.724 | 0.56 | | |
| 10 | 1.354 | 0.95 | 1.43875 | 94.66 |
| 11 | −1.037 | 0.30 | 1.95906 | 17.47 |
| 12 | −6.368 | 0.78 | | |
| 13 | 1.150 | 0.70 | 1.51633 | 64.14 |
| 14 | ∞ | 0.35 | 1.50510 | 63.26 |
| 15 | ∞ | 0 | | |
| Image plane | ∞ | | | |

Aspheric surface data

2nd surface
k = −3.606
A4 = 2.18055e+00, A6 = −4.15320e+00, A8 = 5.59144e+00
5th surface
k = 0.000
A4 = −1.86145e−01, A6 = −1.01348e−01, A8 = 1.86191e+00,
A10 = −2.92552e+00, A12 = 1.91634e+00
6th surface
k = 0.000
A4 = −1.39183e−01, A6 = 9.55772e−02, A8 = 2.31566e−01

| Various data | | |
| --- | --- | --- |
| | far distance | near distance |
| f | 0.48 | 0.47 |
| Fno | 3.62 | 3.62 |
| OBJ | 13.0 | 2.7 |
| Angle of view 2ω | 135.20 | 136.65 |
| d4 | 0.45 | 0.65 |
| d6 | 1.15 | 0.95 |

| Focal length of each unit | | |
| --- | --- | --- |
| f1 = −0.59 | f2 = 12.96 | f3 = 2.25 |

Numerical Example 3

| Unit mm | | | | |
|---|---|---|---|---|
| Surface data | | | | |

| Surface no. | r | d | nd | νd |
|---|---|---|---|---|
| 1 | ∞ | 0.20 | 1.88300 | 40.76 |
| 2* | 0.600 | 0.40 | | |
| 3 | ∞ | 0.30 | 1.49400 | 75.01 |
| 4 | ∞ | variable | | |
| 5* | −1.506 | 0.45 | 1.80610 | 40.92 |
| 6* | −1.511 | variable | | |
| 7(stop) | ∞ | 0.00 | | |
| 8 | 3.179 | 0.60 | 1.81600 | 46.62 |
| 9 | −4.176 | 0.56 | | |
| 10 | 1.729 | 1.00 | 1.57135 | 52.95 |
| 11 | −0.995 | 0.30 | 1.92286 | 18.90 |
| 12 | ∞ | 0.65 | | |
| 13 | 1.146 | 0.70 | 1.51633 | 64.14 |
| 14 | ∞ | 0.35 | 1.50510 | 63.26 |
| 15 | ∞ | 0 | | |
| Image plane | ∞ | | | |

Aspheric surface data

2nd surface
k = −0.672
5th surface
k = 0.000
A4 = −3.30168e−01, A6 = 1.36940e−01, A8 = −7.41702e−01,
A10 = −1.96539e+00
6th surface
k = 0.000
A4 = −1.40109e−01, A6 = 3.80112e−02, A8 = −2.40209e−01

| Various data | | |
|---|---|---|
| | far distance | near distance |
| f | 0.48 | 0.47 |
| Fno | 3.68 | 3.68 |
| OBJ | 10.00 | 2.65 |
| Angle of view 2ω | 131.91 | 134.89 |
| d4 | 0.53 | 0.73 |
| d6 | 1.15 | 0.95 |

| Focal length of each unit | | |
|---|---|---|
| f1 = −0.68 | f2 = 14.27 | f3 = 2.10 |

Numerical Example 4

| Unit mm | | | | |
|---|---|---|---|---|
| Surface data | | | | |

| Surface no. | r | d | nd | νd |
|---|---|---|---|---|
| 1 | ∞ | 0.20 | 1.88300 | 40.76 |
| 2* | 0.532 | 0.42 | | |
| 3 | ∞ | 0.30 | 1.49400 | 75.01 |
| 4 | ∞ | variable | | |
| 5* | −17.674 | 0.45 | 1.80610 | 40.92 |
| 6* | −6.158 | variable | | |
| 7(stop) | ∞ | 0.00 | | |
| 8 | 3.635 | 0.50 | 1.83400 | 37.16 |
| 9 | −3.277 | 0.56 | | |
| 10 | 1.378 | 0.95 | 1.43875 | 94.66 |
| 11 | −1.092 | 0.30 | 1.95906 | 17.47eb;normal |
| 12 | −6.368 | 0.80 | | |
| 13 | 1.319 | 0.70 | 1.51633 | 64.14 |
| 14 | ∞ | 0.35 | 1.50510 | 63.26 |

-continued

| Unit mm | | |
|---|---|---|
| 15 | ∞ | 0 |
| Image plane | ∞ | |

Aspheric surface data

2nd surface
k = −3.372
A4 = 1.64630e+00, A6 = −2.92809e+00, A8 = 3.44475e+00
5th surface
k = 0.000
A4 = −2.58176e−01, A6 = 3.60095e−01, A8 = −3.91154e+00,
A10 = 1.57092e+01, A12 = −1.57970e+01
6th surface
k = 0.000
A4 = −1.09866e−01, A6 = −4.34314e−01, A8 = 1.26895e+00

| Various data | | |
|---|---|---|
| | far distance | near distance |
| f | 0.48 | 0.48 |
| Fno | 3.67 | 3.67 |
| OBJ | 13.00 | 2.7 |
| Angle of view 2ω | 124.01 | 124.01 |
| d4 | 0.45 | 0.65 |
| d6 | 1.28 | 1.08 |

| Focal length of each unit | | |
|---|---|---|
| f1 = −0.60 | f2 = 11.45 | f3 = 2.16 |

Numerical Example 5

| Unit mm | | | | |
|---|---|---|---|---|
| Surface data | | | | |

| surface no. | r | d | nd | νd |
|---|---|---|---|---|
| 1 | ∞ | 0.20 | 1.88300 | 40.76 |
| 2* | 0.531 | 0.42 | | |
| 3 | ∞ | 0.30 | 1.49400 | 75.01 |
| 4 | ∞ | variable | | |
| 5* | −11.101 | 0.45 | 1.80610 | 40.92 |
| 6* | −4.976 | variable | | |
| 7(stop) | ∞ | 0.00 | | |
| 8 | 3.415 | 0.50 | 1.83400 | 37.16 |
| 9 | −3.228 | 0.56 | | |
| 10 | 1.308 | 0.95 | 1.43875 | 94.66 |
| 11 | −1.069 | 0.30 | 1.95906 | 17.47 |
| 12 | −9.063 | 0.65 | | |
| 13 | 1.239 | 0.70 | 1.51633 | 64.14 |
| 14 | ∞ | 0.35 | 1.50510 | 63.26 |
| 15 | ∞ | 0 | | |
| Image plane | ∞ | | | |

Aspheric surface data

2nd surface
k = −3.272
A4 = 1.74333e+00, A6 = −2.89986e+00, A8 = 3.96476e+00
5th surface
k = 0.000
A4 = −2.52401e−01, A6 = 7.21955e−01, A8 = −4.14591e+00,
A10 = 1.50978e+01, A12 = −1.57260e+01

-continued

| Unit mm |
| --- |

6th surface
k = 0.000
A4 = −1.14756e−0, A6 = −1.52522e−01, A8 = 8.36688e−01

| Various data | | |
| --- | --- | --- |
| | far distance | near distance |
| f | 0.48 | 0.47 |
| Fno | 3.59 | 3.58 |
| OBJ | 13.00 | 2.7 |
| Angle of view 2ω | 130.99 | 132.01 |
| d4 | 0.45 | 0.65 |
| d6 | 1.15 | 0.95 |

| Focal length of each unit | | |
| --- | --- | --- |
| f1 = −0.60 | f2 = 10.77 | f3 = 2.01 |

Numerical Example 6

| Unit mm |
| --- |

| Surface data | | | | |
| --- | --- | --- | --- | --- |
| Surface no. | r | d | nd | νd |
| 1 | ∞ | 0.20 | 1.88300 | 40.76 |
| 2* | 0.671 | 0.40 | | |
| 3 | ∞ | 0.30 | 1.49400 | 75.01 |
| 4 | ∞ | variable | | |
| 5* | −2.130 | 0.45 | 1.80610 | 40.92 |
| 6* | −2.120 | variable | | |
| 7(stop) | ∞ | 0.00 | | |
| 8 | 2.498 | 0.60 | 1.80100 | 34.97 |
| 9 | −8.125 | 0.54 | | |
| 10 | 1.615 | 1.00 | 1.58913 | 61.14 |
| 11 | −1.110 | 0.30 | 1.95906 | 17.47 |
| 12 | ∞ | 0.70 | | |
| 13 | 1.279 | 0.70 | 1.51633 | 64.14 |
| 14 | ∞ | 0.35 | 1.50510 | 63.26 |
| 15 | ∞ | 0 | | |
| Image plane | ∞ | | | |

Aspheric surface data

2nd surface
k = −1.272
A4 = 2.52172e−01, A6 = 5.10930e−01, A8 = 1.36394e−02
5th surface
k = 0.000
A4 = −3.31075e−01, A6 = 1.48304e+00, A8 = −6.52969e+00,
A10 = 9.66075e+00
6th surface
k = 0.000
A4 = −1.90525e−01, A6 = 6.30400e−01, A8 = −2.67343e+00,
A10 = 3.83026e+00

| Various data | | |
| --- | --- | --- |
| | far distance | near distance |
| f | 0.50 | 0.49 |
| F no. | 3.97 | 3.96 |
| OBJ | 10.00 | 2.65 |
| Angle of view 2ω | 140.75 | 147.99 |
| d4 | 0.63 | 0.98 |
| d6 | 1.32 | 0.97 |

| Focal length of each unit | | |
| --- | --- | --- |
| f1 = −0.76 | f2 = 26.32 | f3 = 2.10 |

Numerical Example 7

| Unit mm |
| --- |

| Surface data | | | | |
| --- | --- | --- | --- | --- |
| surface no. | r | d | nd | νd |
| 1 | ∞ | 0.20 | 1.88300 | 40.76 |
| 2* | 0.596 | 0.40 | | |
| 3 | ∞ | 0.30 | 1.49400 | 75.01 |
| 4 | ∞ | variable | | |
| 5* | −2.136 | 0.45 | 1.80610 | 40.92 |
| 6* | −1.868 | variable | | |
| 7(stop) | ∞ | 0.00 | | |
| 8 | 20.454 | 0.60 | 1.80100 | 34.97 |
| 9 | −1.915 | 0.25 | | |
| 10 | 1.936 | 0.93 | 1.58913 | 61.14 |
| 11 | −1.110 | 0.30 | 1.95906 | 17.47 |
| 12 | −8.948 | 0.77 | | |
| 13 | 1.270 | 0.70 | 1.51633 | 64.14 |
| 14 | ∞ | 0.35 | 1.50510 | 63.26 |
| 15 | ∞ | 0 | | |
| Image plane | ∞ | | | |

Aspheric surface data

2nd surface
k = −0.525
A4 = −3.04058e−01, A6 = 5.23242e−01, A8 = −1.04713e+00
5th surface
k = 0.000
A4 = −5.35091e−01, A6 = 3.22033e−01, A8 = −3.87574e+00,
A10 = 9.19508e+00
6th surface
k = 0.000
A4 = −2.56439e−01, A6 = −1.20078e+00, A8 = 3.54767e+01,
A10 = −3.65029e+02, A12 = 1.32236e+03

| Various data | | |
| --- | --- | --- |
| | far distance | near distance |
| f | 0.46 | 0.45 |
| Fno | 3.65 | 3.64 |
| OBJ | 10.00 | 2.65 |
| Angle of view 2ω | 136.37 | 138.65 |
| d4 | 0.64 | 0.82 |
| d6 | 0.64 | 0.46 |

| Focal length of each unit | | |
| --- | --- | --- |
| f1 = −0.67 | f2 = 10.49 | f3 = 1.77 |

Values of the conditional expressions of each of examples are shown below:

| | | Example 1 | Example 2 | Example 3 | Example 4 |
| --- | --- | --- | --- | --- | --- |
| (1) | f1/f2 | −0.044 | −0.046 | −0.047 | −0.052 |
| (2) | f1/f3 | −0.303 | −0.265 | −0.321 | −0.278 |
| (3) | f1/d23e | −0.541 | −0.519 | −0.59 | −0.468 |
| (4) | f12e/f3' | −0.464 | −0.435 | −0.52 | −0.436 |
| (5) | r2mf/fe | −7.03 | −15.332 | −3.11 | −36.822 |
| (6) | f3p/f3ce | 0.226 | 0.105 | 0.106 | 0.12 |
| (7) | d3p/d3pce | 0.869 | 0.901 | 1.071 | 0.901 |
| (8) | f23'k/f1 | −2.391 | −2.544 | −2.158 | −2.602 |
| (9) | Δ2/fe | 0.417 | 0.419 | 0.413 | 0.417 |

-continued

| | | | | | |
|---|---|---|---|---|---|
| (10) | (r3pf − r3pr)/<br>(r3pf + r3pr) | −5.805 | −11.029 | −7.382 | 19.293 |
| (11) | (r3cpf − r3cpr)/<br>(r3cpf + r3cpr) | −1.718 | −1.54 | −1 | −1.552 |

| | | Example 5 | Example 6 | Example 7 |
|---|---|---|---|---|
| (1) | f1/f2 | −0.055 | −0.029 | −0.064 |
| (2) | f1/f3 | −0.297 | −0.36 | −0.38 |
| (3) | f1/d23e | −0.522 | −0.572 | −1.057 |
| (4) | f12e/f3' | −0.465 | −0.518 | −0.574 |
| (5) | r2mf/fe | −23.128 | −4.259 | −4.646 |
| (6) | f3p/f3ce | 0.068 | 0.249 | 0.248 |
| (7) | d3p/d3pce | 0.901 | 1.107 | 2.395 |
| (8) | f23'k/f1 | −2.438 | −2.06 | −2.058 |
| (9) | Δ2/fe | 0.417 | 0.696 | 0.393 |
| (10) | (r3pf − r3pr)/<br>(r3pf + r3pr) | 35.477 | −1.888 | 1.207 |
| (11) | (r3cpf − r3cpr)/<br>(r3cpf + r3cpr) | −1.337 | −1 | −1.552 |

Figure 16:
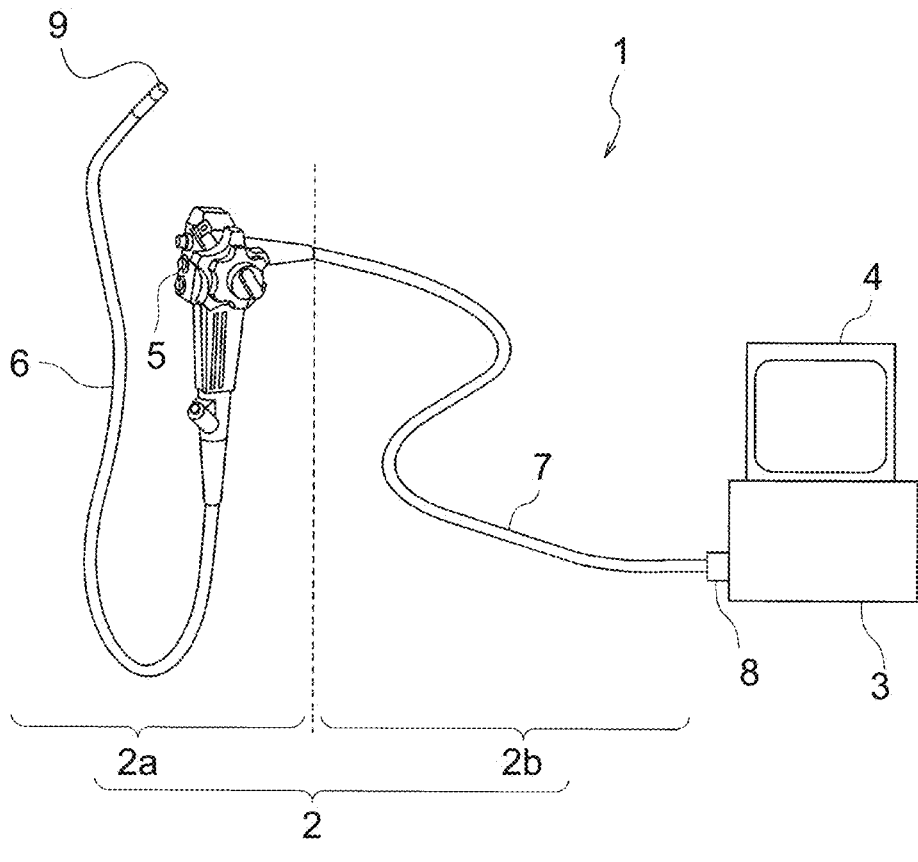
FIG. 16 is a diagram showing an endoscope system, wherein the endoscope is shown in an enlarged manner to better show its structure.

FIG. 16 is a diagram showing an endoscope system. In FIG. 16, the endoscope is illustrated in an enlarged manner to show its structure.

The endoscope system 1 includes an endoscope 2 and an image processing apparatus 3. The endoscope 2 includes a scope unit 2a and a connection cord 2b. The image processing apparatus 3 is connected with a display unit 4.

The scope unit 2a has an operation part 5 and an insert part 6. The insert part 6 is a thin, long part that can be inserted into a body cavity of a patient. The insert part 6 is made of a flexible component. The observer or operator can perform various operations using an angle knob and other parts of the operation part 5.

The connection cord 2b extends from the operation part 5. The connection cord 2b includes a universal cord 7. The universal cord 7 is connected to the image processing apparatus 3 via a connector 8.

The universal cord 7 is used to transmit and receive various signals. The signals include a power voltage signal and a CCD drive signal, which are transmitted from a power source and a video processor provided in the image processing apparatus 3 to the scope unit 2a. The signals also include an image signal, which is transmitted from the scope part 2a to the video processor.

The video processor in the image processing apparatus 3 can be connected with peripheral devices such as a video printer (not shown). The video processor applies image processing on the image signal transmitted from the scope part 2a. The display unit 4 displays an endoscope image based on the video signal on its screen.

The distal end 9 of the insert part 6 is provided with an optical system (not shown). This optical system uses the endoscope objective optical system according to the embodiment.

As above, the present invention can be suitably applied to an endoscope objective optical system that is desired to have high imaging performance when focused regardless of the object distance while being small in size and an endoscope that is desired to capture clear images regardless of the object distance.

According to the present invention, it is possible to provide an endoscope objective optical system that has high imaging performance when focused regardless of the object distance while being small in size and an endoscope that can capture clear images regardless of the object distance.

What is claimed is:

1. An objective optical system for an endoscope comprising, in order from the object side: a first lens unit having a negative refractive power; a second lens unit having a positive refractive power; and a third lens unit having a positive refractive power, wherein the first lens unit includes a negative lens, the second lens unit includes a positive meniscus lens having a convex surface facing the image side, the third lens unit includes, in order from the object side, an object side positive lens and a cemented lens made up of a positive lens and a negative lens, the second lens unit is moved for focusing, and the objective optical system for an endoscope satisfies the following conditional expressions (1) and (2): −0.07<f1/f2<−0.015 (1), −0.4<f1/f3<−0.15 (2), where f1 is the focal length of the first lens unit, f2 is the focal length of the second lens unit, and f3 is the focal length of the third lens unit.

2. An objective optical system for an endoscope according to claim 1, satisfying the following conditional expression (3):

$$-1.13 < f1/d23e < -0.4, \qquad (3)$$

where f1 is the focal length of the first lens unit, and d23e is the distance between the second lens unit and the third lens unit in the state in which the optical system is focused on an object at a far distance.

3. An objective optical system for an endoscope according to claim 1, satisfying the following conditional expression (4):

$$-0.59 < f12e/f3' < -0.35, \qquad (4)$$

where f12e is the combined focal length of the first lens unit and the second lens unit in the state in which the optical system is focused on an object at a far distance, and f3' is the combined focal length of the object side positive lens and the cemented lens.

4. An objective optical system for an endoscope according to claim 1, satisfying the following conditional expression (5):

$$-50 < r2mf/fe < -2.5, \qquad (5)$$

where r2mf is the radius of curvature of the object side surface of the positive meniscus lens, and fe is the focal length of the objective optical system in the state in which it is focused on an object at a far distance.

5. An objective optical system for an endoscope according to claim 1, satisfying the following conditional expression (6):

$$0.01 < f3p/f3ce < 0.3, \qquad (6)$$

where f3p is the focal length of the object side positive lens, and f3ce is the focal length of the cemented lens.

6. An objective optical system for an endoscope according to claim 1, satisfying the following conditional expression (7):

$$0.5 < d3p/d3pce < 3, \tag{7}$$

where d3p is the thickness of the object side positive lens, and d3pce is the distance between the object side positive lens and the cemented lens.

7. An objective optical system for an endoscope according to claim 1, satisfying the following conditional expression (8):

$$-3 < f23'k/f1 < -2, \tag{8}$$

where f23'k is the focal length of a group of lenses including the second lens unit, the object side positive lens, and the cemented lens in the state in which the optical system is focused on an object at a near distance, and f1 is the focal length of the first lens unit.

8. An objective optical system for an endoscope according to claim 1, satisfying the following conditional expression (9):

$$0.38 < \Delta2/fe < 0.8, \tag{9}$$

where $\Delta2$ is the amount of movement of the second lens unit, and fe is the focal length of the objective optical system for an endoscope in the state in which it is focused on an object at a far distance.

9. An objective optical system for an endoscope according to claim 1, satisfying the following conditional expression (10):

$$-18 < (r3pf - r3pr)/(r3pf + r3pr) < 40, \tag{10}$$

where r3pf is the radius of curvature of the object side surface of the object side positive lens, and r3pr is the radius of curvature of the image side surface of the object side positive lens.

10. An objective optical system for an endoscope according to claim 1, satisfying the following conditional expression (11):

$$-2.15 < (r3cpf - r3cpr)/(r3cpf + r3cpr) < -1, \tag{11}$$

where r3cpf is the radius of curvature of the object side surface of the cemented lens, and r3cpr is the radius of curvature of the image side surface of the cemented lens.

11. An objective optical system for an endoscope according to claim 1, wherein the third lens unit further includes an image side positive lens disposed on the image side of the cemented lens.

12. An objective optical system for an endoscope according to claim 1 further comprising an aperture stop disposed on the object side of the third lens unit.

13. An endoscope comprising an objective optical system for an endoscope according to claim 1.

* * * * *